US010369131B2

(12) United States Patent
Tepper et al.

(10) Patent No.: US 10,369,131 B2
(45) Date of Patent: *Aug. 6, 2019

(54) ULTRAPURE TETRAHYDROCANNABINOL-11-OIC ACIDS

(71) Applicant: Corbus Pharmaceuticals, Inc., Norwood, MA (US)

(72) Inventors: Mark Tepper, Newton, MA (US); Dean A. Frey, Edwardsville, IL (US); David Goeddel, Madison, WI (US); Karl E. Reineke, Placitas, NM (US)

(73) Assignee: Corbus Pharmaceuticals, Inc., Norwood, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/198,381

(22) Filed: Nov. 21, 2018

(65) Prior Publication Data

US 2019/0091200 A1 Mar. 28, 2019

Related U.S. Application Data

(60) Continuation of application No. 15/698,544, filed on Sep. 7, 2017, now Pat. No. 10,154,986, which is a continuation of application No. 15/347,059, filed on Nov. 9, 2016, now Pat. No. 9,801,849, which is a division of application No. 14/546,116, filed on Nov. 18, 2014, now abandoned, which is a continuation of application No. PCT/US2014/016050, filed on Feb. 12, 2014, said application No. 15/698,544 is a continuation of application No. 15/347,104, filed on Nov. 9, 2016, now Pat. No. 9,820,964, which is a division of application No. 14/546,116, filed on Nov. 18, 2014, now abandoned, said application No. 15/698,544 is a continuation of application No. 15/220,127, filed on Jul. 26, 2016, now Pat. No. 10,085,964, which is a continuation of application No. 14/546,116, filed on Nov. 18, 2014, now abandoned.

(60) Provisional application No. 61/837,743, filed on Jun. 21, 2013, provisional application No. 61/763,630, filed on Feb. 12, 2013.

(51) Int. Cl.
*A61K 31/352* (2006.01)
*A61K 9/00* (2006.01)

(52) U.S. Cl.
CPC ............ *A61K 31/352* (2013.01); *A61K 9/007* (2013.01); *A61K 9/0014* (2013.01); *A61K 9/0019* (2013.01); *A61K 9/0048* (2013.01); *A61K 9/0053* (2013.01)

(58) Field of Classification Search
CPC .. A61K 31/352; A61K 9/0019; A61K 9/0014; A61K 9/007; A61K 9/0053; A61K 9/0048
See application file for complete search history.

(56) References Cited

U.S. PATENT DOCUMENTS

| | | |
|---|---|---|
| 4,880,830 A | 11/1989 | Rhodes |
| 5,338,753 A | 8/1994 | Burstein et al. |
| 6,974,835 B2 | 12/2005 | Burstein et al. |
| 7,413,748 B2 | 8/2008 | Reidenberg et al. |
| 7,553,863 B2 | 6/2009 | Reardan et al. |
| 8,044,071 B2 | 10/2011 | Carroll |
| 9,820,964 B2 | 11/2017 | Tepper |
| 10,154,986 B2 * | 12/2018 | Tepper ................. A61K 31/352 |
| 2004/0110827 A1 | 6/2004 | Aviv et al. |
| 2004/0143126 A1 | 7/2004 | Webster et al. |
| 2004/0186166 A1 | 9/2004 | Burstein et al. |
| 2005/0009903 A1 | 1/2005 | Martin et al. |
| 2005/0070596 A1 | 3/2005 | Baker et al. |
| 2006/0009528 A1 | 1/2006 | Kozlowski et al. |
| 2007/0037873 A1 | 2/2007 | Zurier et al. |
| 2007/0060636 A1 | 3/2007 | Aviv et al. |
| 2007/0060639 A1 | 3/2007 | Wermeling |
| 2007/0099988 A1 | 5/2007 | Sandage |
| 2007/0104741 A1 | 5/2007 | Murty et al. |
| 2009/0075875 A1 | 3/2009 | Hoffman et al. |
| 2010/0035978 A1 | 2/2010 | Guy et al. |
| 2011/0274703 A1 | 11/2011 | Agarwal et al. |
| 2011/0301078 A1 | 12/2011 | Schetz et al. |
| 2012/0289589 A1 | 11/2012 | Travis |
| 2012/0309820 A1 | 12/2012 | Zurier et al. |
| 2013/0338220 A1 | 12/2013 | Tepper et al. |
| 2015/0141501 A1 | 5/2015 | Tepper |
| 2016/0367518 A1 | 12/2016 | Zurier et al. |
| 2017/0022179 A1 | 1/2017 | Tepper et al. |
| 2017/0071898 A1 | 3/2017 | Tepper |
| 2017/0071899 A1 | 3/2017 | Tepper |
| 2017/0071900 A1 | 3/2017 | Tepper |
| 2018/0116999 A1 | 5/2018 | Zurier et al. |

FOREIGN PATENT DOCUMENTS

| | | |
|---|---|---|
| JP | 2008-543800 A | 12/2008 |
| WO | WO-2004/058251 A1 | 7/2004 |
| WO | WO-2004/100893 A2 | 11/2004 |
| WO | WO-2006/133941 A2 | 12/2006 |
| WO | WO-2012/048045 A1 | 4/2012 |
| WO | WO-2012/170290 A1 | 12/2012 |
| WO | WO-2014/127016 A2 | 8/2014 |

OTHER PUBLICATIONS https://www.ninds.nih.gov/Disorders/All-Disorders/Dermatomyositis-Information-Page; (2018) accessed online Feb. 11, 2019.*
U.S. Appl. No. 15/619,089, Zurier et al.

(Continued)

*Primary Examiner* — John M Mauro
(74) *Attorney, Agent, or Firm* — Clark & Elbing LLP

(57) ABSTRACT

This application is in the field of medicinal chemistry and relates to ultrapure ajulemic acid, its synthesis, pharmaceutical compositions and methods of use thereof for the treatment and/or prevention of inflammation, pain, and fibrotic diseases including scleroderma, systemic sclerosis, scleroderma-like disorders, sine scleroderma, liver cirrhosis, interstitial pulmonary fibrosis, idiopathic pulmonary fibrosis, Dupuytren's contracture, keloids, chronic kidney disease, chronic graft rejection, and other scarring-wound healing abnormalities, post-operative adhesions, and reactive fibrosis.

16 Claims, 18 Drawing Sheets

(56) References Cited

OTHER PUBLICATIONS

"Fibrosis in systemic sclerosis: emerging concepts and implications for targeted therapy", available in PMC Apr. 24 2014, published in final edited form as: Autoimmun Rev 10(5):267-75 (2011) (22 pages).
Akhmetshina et al., "The cannabinoid receptor CB2 exerts antifibrotic effects in experimental dermal fibrosis", Arthritis Rheum 60(4):1129-36 (2009).
Akhmetshina et al., "Treatment with imatinib prevents fibrosis in different preclinical models of systemic sclerosis and induces regression of established fibrosis", Arthritis Rheum 60(1):219-24 (2009).
Ambrosio et al., "Ajulemic acid, a synthetic nonpsychoactive cannabinoid acid, bound to the ligand binding domain of the human peroxisome proliferator-activated receptor gamma," J Biol Chem. 282(25):18625-33 (2007).
Anandakandah, "Manthana Bhairava," T.M.S.S.M. Library, Tanjore, Madras, pp. 9-13 (1952).
Avouac et al., "Inhibition of activator protein 1 signaling abrogates transforming growth factor beta-mediated activation of fibroblasts and prevents experimental fibrosis", Arthritis Rheum 64(5):1642-52 (2012).
Balistreri et al., "The cannabinoid WIN55, 212-2 abrogates dermal fibrosis in scleroderma bleomycin model", Ann Rheum Dis. 70(4):695-9 (2011).
Batista et al., "Determination of ajulemic acid and its glucuronide in human plasma by gas chromatography-mass spectrometry," J Chromatogr B Analyt Technol Biomed Life Sci. 820(1):77-82 (2005).
Beyer et al., "Animal models of systemic sclerosis: prospects and limitations", Arthritis Rheum. 62(10):2831-44 (2010).
Brownjohn et al., "Cannabinoids and neuropathic pain," Neuro. Pain. 79-102 (2012).
Burstein et al., "Ajulemic acid: A novel cannabinoid produces analgesia without a 'high'," Life Sci. 75(12):1513-22 (2004).
Burstein et al., "Cannabinoids, endocannabinoids, and related analogs in inflammation," AAPS J. 11(1):109-19 (2009).
Burstein et al., "Isolation and characterization of two major urinary metabolites of delta1-tetrahydrocannabinol," Science. 176(4033):422-3 (1972).
Burstein et al., "Synthetic nonpsychotropic cannabinoids with potent antiinflammatory, analgesic, and leukocyte antiadhesion activities," J Med Chem. 35(17):3135-41 (1992).
Burstein, "Ajulemic acid (IP-751): synthesis, proof of principle, toxicity studies, and clinical trials," AAPS J. 7(1):E143-8 (2005).
Buzzi et al., "The antimigraine drug, sumatriptan (GR43175), selectively blocks neurogenic plasma extravasation from blood vessels in dura mater" British Journal of Pharmacology 99(1):202-6 (1990).
Cheng et al., "Relationship between the inhibition constant (K1) and the concentration of inhibitor which causes 50 per cent inhibition (I50) of an enzymatic reaction," Biochem Pharmacol. 22(23):3099-108 (1973).
Chung et al., "Segmental spinal nerve ligation model of neuropathic pain", Methods Mal. Med. 99:35-45 (2004).
Compton et al., "Aminoalkylindole analogs: cannabimimetic activity of a class of compounds structurally distinct from delta 9-tetrahydrocannabinol," J Pharmacol Exp Ther. 263(3):1118-26 (1992).
Compton et al., "Pharmacological profile of a series of bicyclic cannabinoid analogs: classification as cannabimimetic agents," J Pharmacol Exp Ther. 260(1):201-9 (1992).
Dajani et al., "1',1'-Dimethylheptyl-delta-8-tetrahydrocannabinol-11-oic acid: a novel, orally effective cannabinoid with analgesic and anti-inflammatory properties," J Pharmacol Exp Ther. 291(1):31-8 (1999).
Davies et al., "Antibody-antigen complexes," Annu Rev Biochem. 59:439-73 (1990).
Dyson et al., "Antihyperalgesic properties of the cannabinoid CT-3 in chronic neuropathic and inflammatory pain states in the rat," Pain. 116(1-2):129-37 (2005).
Flörke et al., "Silica" Encyclopedia of Industrial Chemistry. 32:421-507 (2008).
Garcia-Gonzalez et al., "Cannabinoids inhibit fibrogenesis in diffuse systemic sclerosis fibroblasts", Rheumatology 48(9):1050-6 (2009).
Genovese et al., "Effect of rosiglitazone and 15-deoxy-Delta12, 14-prostaglandin J2 on bleomycin-induced lung injury", Eur Respir J 25(2):225-34 (2005).
Ghosh et al., "Peroxisome proliferator-activated receptor-gamma abrogates Smad-dependent collagen stimulation by targeting the p300 transcriptional coactivator," FASEB J. 23(9):2968-77 (2009).
Gonzalez et al., "Synthetic cannabinoid ajulemic acid exerts potent antifibrotic effects in experimental models of systemic sclerosis," Ann Rheum Dis. 71(9):1545-51 (2012).
Gonzalez et al., "The synthetic cannabinoid ajulemic acid targets scleroderma fibrosis," Arthritis and Rheumatism 62(Suppl 10):615 (2010). Abstract only.
Griffin et al., "Evaluation of cannabinoid receptor agonists and antagonists using the guanosine-5'-O-(3[35S]thio)-triphosphate binding assay in rat cerebellar membranes," J Pharmacol Exp Ther. 285(2):553-60 (1998).
Hill et al., "Enhancement of anxiety-like responsiveness to the cannabinoid CB(1) receptor agonist HU-210 following chronic stress," Eur J Pharmacol. 499(3):291-5 (2004).
Hiragata et al., "Effects of IP-751, ajulemic acid, on bladder overactivity induced by bladder irritation in rats," Urology. 70(1):202-8 (2007).
Honore et al., "A-425619 [1-isoquinolin-5-yl-3-(4-trifluoromethyl-benzyl)-urea], a novel transient receptor potential type V1 receptor antagonist, relieves pathophysiological pain associated with inflammation and tissue injury in rats", J Pharmacol Exp Ther 314(1):410-21 (2005).
International Search Report and Written Opinion for International Patent Application No. PCT/US14/16050, dated May 19, 2014 (8 pages).
International Search Report for International Application No. PCT/US12/40380, dated Aug. 17, 2012 (2 pages).
International Search Report for International Application No. PCT/US2011/054985, dated Feb. 8, 2012 (3 pgs).
Johnson et al., "Suppression of fibroblast metalloproteinases by ajulemic acid, a nonpsychoactive cannabinoid acid," J Cell Biochem. 100(1):184-90 (2007).
Jones et al., "Clinical studies of cannabis tolerance and dependence," Ann N.Y. Acad Sci. 282:221-39 (1976).
Jones et al., "Systemic gabapentin and S(+)-3-isobutyl-gamma-aminobutyric acid block secondary hyperalgesia", Brain Res. 810(1-2):93-9 (1998).
Juarez-Rojas et al., "Pioglitazone improves the cardiovascular profile in patients with uncomplicated systemic lupus erythematosus: a double-blind randomized clinical trial," Lupus. 21(1):27-35 (2012).
Jun et al., "The effect of intrathecal gabapentin and 3-isobutyl gamma-aminobutyric acid on the hyperalgesia observed after thermal injury in the rat", Anesth Analg. 86(2):348-54 (1998).
Kapoor et al., "Loss of peroxisome proliferator-activated receptor gamma in mouse fibroblasts results in increased susceptibility to bleomycin-induced skin fibrosis", Arthritis Rheum 60(9):2822-9 (2009).
Karst et al., "Analgesic effect of the synthetic cannabinoid CT-3 on chronic neuropathic pain: a randomized controlled trial," JAMA. 290(13):1757-62 (2003).
Karst, "Comments on cannabimimetic properties of ajulemic acid", J Pharmacol Exp Ther 322(1):420-1 (2007).
Khan, "Khazaain-al-Advia, vol. 1," Ghani Nadeem Yunus Printer / Sheikh Mohd Basheer & Sons, Lahore, pp. 4-8 (1911).
Kim et al., "An Experimental Model for Peripheral Neuropathy Produced by Segmental Spinal Nerve Ligation in the Rat," *Pain* 50(3):355-363 (1992).
Kitchen et al., "Differential effects of di-isopropylfluorophosphate poisoning and its treatment on opioid antinociception in the mouse," Life Sci. 33(Suppl 1):669-72 (1983).

(56) References Cited

OTHER PUBLICATIONS

Klein, "Cannabinoid-based drugs as anti-inflammatory therapeutics", Nat Rev Immunol 5(5):400-11 (2005).
Klingsberg et al., "Current clinical trials for the treatment of idiopathic pulmonary fibrosis," Respirology 15(1):19-31 (2010).
Kulkarni et al., "PPAR-gamma ligands repress TGFbeta-induced myofibroblast differentiation by targeting the PI3K/Akt pathway: implications for therapy of fibrosis", PLoS One 6(1):e15909 (2011) (11 pages).
Leroy, "Increased collagen synthesis by scleroderma skin fibroblasts in vitro: a possible defect in the regulation or activation of the scleroderma fibroblast," J Clin Invest. 54(4):880-9 (1974).
Liu et al., "Activation and binding of peroxisome proliferator-activated receptor gamma by synthetic cannabinoid ajulemic acid", Mol Pharmacol 63(5):983-92 (2003).
Lucattelli et al., "Ajulemic acid exerts potent anti-fibrotic effect during the fibrogenic phase of bleomycin lung," Respir Res. 17(1):49 (2016) (16 pages).
Malmqvist, "Biospecific interaction analysis using biosensor technology," Nature. 361(6408):186-7 (1993).
Marquart et al., "Inactivation of the cannabinoid receptor CB1 prevents leukocyte infiltration and experimental fibrosis", Arthritis Rhem 62(11):3467-76 (2010).
Martin et al., "Behavioral, biochemical, and molecular modeling evaluations of cannabinoid analogs," 40(3):471-8 (1991).
Masi et al., "Preliminary criteria for the classification of systemic sclerosis (scleroderma). Subcommittee for scleroderma criteria of the American Rheumatism Association Diagnostic and Therapeutic Criteria Committee" Arthritis Rheum 23(5):581-90 (1980).
McGaraughty et al., "Effects of A-317491, a novel and selective P2X3/P2X2/3 receptor antagonist, on neuropathic, inflammatory and chemogenic nociception following intrathecal and intraplantar administration", British Journal of Pharmacology 140(8):1381-8 (2003).
McPartland et al., "Meta-analysis of cannabinoid ligand binding affinity and receptor distribution: interspecies differences," Br J Pharmacol. 152(5):583-93 (2007).
Michalski et al., "Cannabinoids reduce markers of inflammation and fibrosis in pancreatic stellate cells", PLoS One 3(2):e1701 (2008) (12 pages).
Milam et al., "PPAR-gamma agonists inhibit profibrotic phenotypes in human lung fibroblasts and bleomycin-induced pulmonary fibrosis," Am J Physiol Lung Cell Mol Physiol. 294(5):L891-901 (2008).
Mullin, J.W., "Crystallization and precipitation," Ull. Ency. of Indust. Chem. 582-630 (2002).
Nagakura et al., "Allodynia and hyperalgesia in adjuvant-induced arthritic rats: time course of progression and efficacy of analgesics", J Pharmacol Exp Ther 306(2):490-7 (2003).
Nozaki-Taguchi et al., "A novel model of primary and secondary hyperalgesia after mild thermal injury in the rat", Neurosci Lell. 254(1):25-8 (1998).
O'Sullivan, "Cannabinoids go nuclear: evidence for activation of peroxisome proliferator-activated receptors", Br J Pharmacol 152(5):576-82 (2007).
Ofek et al., "Peripheral cannabinoid receptor, CB2, regulates bone mass," Proc Natl Acad Sci U S A. 103(3):696-701 (2006).
Parker et al., "Suppression of human macrophage interleukin-6 by a nonpsychoactive cannabinoid acid," Rheumatol Int. 28(7):631-5 (2008) (5 pages).
Pertwee et al., "International Union of Basic and Clinical Pharmacology. LXXIX. Cannabinoid receptors and their ligands: beyond CB1 and CB2," Pharmacol Rev. 62(4):588-631 (2010).
Pertwee, "Emerging strategies for exploiting cannabinoid receptor agonists as medicines", Br J Pharmacol 156(3):397-411 (2009).
Pertwee, "Pharmacological actions of cannabinoids," Handb Exp Pharmacol. (168):1-51 (2005).
Pertwee, "The ring test: a quantitative method for assessing the 'cataleptic' effect of cannabis in mice," Br J Pharmacol. 46(4):753-63 (1972).

Recht et al., "Antitumor effects of ajulemic acid (CT3), a synthetic non-psychoactive cannabinoid," Biochem Pharmacol. 62(6):755-63 (2001).
Reich et al. "The transcription factor Fra-2 regulates the production of extracellular matrix in systemic sclerosis", Arthritis Rheum 62(1):280-90 (2010).
Rhee et al., "Cannabinol derivatives: binding to cannabinoid receptors and inhibition of adenylylcyclase," J Med Chem. 40(20):3228-33 (1997).
Rockey et al., "Fibrosis—a common pathway to organ injury and failure," N Eng J Med. 372(12):1138-49 (2015).
Rowe et al., "Handbook of pharmaceutical excipients," Pharm Press and APhA. (2009) (917 pages).
Saa et al., "Deoxygenation of highly hindered phenols," J Org Chem. 55(3):991-5 (1990).
Salim et al., "Pain measurements and side effect profile of the novel cannabinoid ajulemic acid," Neuropharmacology 48(8):1164-71 (2005).
Servettaz et al., "Targeting the cannabinoid pathway limits the development of fibrosis and autoimmunity in a mouse model of systemic sclerosis", Am J Pathol 177(1):187-96 (2010).
Sharma, "Priyanighantu," Chaukhamba Surabharti Prakashana, Varanasi, pp. 14-18 (2004).
Shekunov et al., "Crystallization processes in pharmaceutical technology and drug delivery design," J Cryst Growth. 211(1):122-36 (2000).
Smith et al., "The effect of plasma protein binding on in vivo efficacy: misconceptions in drug discovery," Nat Rev Drug Discov. 9(12):929-39 (2010).
Stebulis et al., "Ajulemic acid, a synthetic cannabinoid acid, induces an antiinflammatory profile of eicosanoids in human synovial cells," Life Sci. 83(19-20):666-70 (2008).
Strassman et al., "Sensitization of meningeal sensory neurons and the origin of headaches", Nature 384(6609) :560-4 (1996).
Supplementary European Search Report for European Patent Application No. 12796691.9, dated Jan. 16, 2015 (8 pages).
Teixeira-Clerc et al., "Le systeme endocannabinoide, une nouvelle cible pour le traitement de la fibrose hepatique", Pathol Biol 56(1):36-38 (2008). Abstract only.
Tepper et al., "Highly Purified Ajulemic Acid is a CB2 Agonist with Reduced CB1 Activity," 23rd Annual Symposium on Cannabinoids, International Cannabinoid Research Society (Mar. 2013) (Abstract only).
Tepper et al., "Ultrapure ajulemic acid has improved CB2 selectivity with reduced CB1 activity," Bioorg Med Chem. 22(13):3245-51 (2014).
Thannickal et al., "Mechanisms of pulmonary fibrosis," Annu Rev Med. 55:395-417 (2004).
The Advisory Committee Briefing Document—Preclinical Pharmacology and Toxicology Summary for Pargluva (2005) (12 pages).
Tyagi et al., "Functional role of cannabinoid receptors in urinary bladder," Indian J Urol. 26(1): 26-35 (2010) (20 pages).
Valenzano et al., "Pharmacological and pharmacokinetic characterization of the cannabinoid receptor 2 agonist, GW405833, utilizing rodent models of acute and chronic pain, anxiety, ataxia and catalepsy", Neuropharmacology 48(5):658-72 (2005).
Vann et al., "Cannabimimetic properties of ajulemic acid", J Pharmacol Exp Ther 320(2):678-86 (2007).
Varga et al., "Systemic sclerosis: a prototypic multisystem fibrotic disorder", J Clin Invest 117 (3):557-67 (2007).
Venalis et al., "Lack of inhibitory effects of the anti-fibrotic drug imatinib on endothelial cell functions in vitro and in vivo", J Cell Mol Med 13(10):4185-91 (2009).
Voscopoulos et al., "When does acute pain become chronic?" Br J Anaesth. 105(Suppl 1):i69-85 (2010).
Walker et al., "The VR1 antagonist capsazepine reverses mechanical hyperalgesia in models of inflammatory and neuropathic pain", J Pharmacol Exp Ther 304(1):56-62 (2003).
Wang et al., "Facile deoxygenation of phenols and enols using sodium borohydride-nickel chloride," J Chem Soc. 15:1897-1900 (1992).

(56) References Cited

OTHER PUBLICATIONS

Wei et al., "PPARgamma downregulation by TGFbeta in fibroblast and impaired expression and function in systemic sclerosis: a novel mechanism for progressive fibrogenesis", PLoS One 5(11):e13778 (2010) (13 pages).
Welch et al., "Reduction of aryl diethyl phosphates with titanium metal: a method for deoxygenation of phenols," J Org Chem. 43(25):4797-99 (1978).
Wieland et al., "Measurement of receptor-stimulated guanosine 5'-O-(gamma-thio)triphosphate binding by G proteins," Methods Enzymol. 237:3-13 (1994).
Wiley et al., "Cannabinoid pharmacological properties common to other centrally acting drugs," Eur J Pharmacol. 471(3):185-93 (2003).
Wiley et al., "Structural and pharmacological analysis of O-2050, a putative neutral cannabinoid CB(1) receptor antagonist," available in PMC Jan. 25, 2012, published in final edited form as: Eur J Pharmacol. 651(1-3):96-105 (2011) (21 pages).
Wiley et al., "Structure-activity relationships of indole- and pyrrole-derived cannabinoids," J Pharmacol Exp Ther. 285(3):995-1004 (1998).
Wiley et al., "Synthesis and pharmacology of 1-alkyl-3-(1-naphthoyl)indoles: steric and electronic effects of 4- and 8-halogenated naphthoyl substituents," Bioorg Med Chem. 20(6):2067-81 (2012).
Wiley, "Ajulemic acid," IDrugs 8(12):1002-11 (2005) (10 pages).
Xanthos et al., "Animal models of Chronic Pain: Chronic post-ischemia pain: a novel animal model of Complex Regional Pain Syndrome Type I produced by prolonged hindpaw ischemia and reperfusion in the rat", J Pain 5(3):1 (2004). Abstract only.
Yaksh et al., "An automated flinch detecting system for use in the formalin nociceptive bioassay", Journal of Applied Physiology 90(6):2386-402 (2001).
Yamamoto, "Animal model of systemic sclerosis", J Dermatol 37(1):26-41 (2010).
Zurier et al., "Ajulemic acid, a synthetic cannabinoid, increases formation of the endogenous proresolving and anti-inflammatory eicosanoid, lipoxin A4," FASEB J. 23(5):1503-9 (2009).
Zurier et al., "Cannabinoids, inflammation, and fibrosis," FASEB J. 30(11):3682-9 (2016).
Zurier et al., "Dimethylheptyl-THC-11 oic acid: a nonpsychoactive antiinflammatory agent with a cannabinoid template structure," Arthritis Rheum. 41(1):163-70 (1998).
Zurier et al., "Suppression of human monocyte interleukin-1beta production by ajulemic acid, a nonpsychoactive cannabinoid," Biochem Pharmacol. 65(4):649-55 (2003).
Zurier, "Prospects for cannabinoids as anti-inflammatory agents," J Cell Biochem. 88(3):462-6 (2003).
International Preliminary Report on Patentability for International Application No. PCT/US2017/030236, dated Oct. 30, 2018 (10 pages).
International Search Report and Written Opinion for International Application No. PCT/US2017/030236, dated Jul. 26, 2017 (17 pages).

* cited by examiner

FIGURE 1
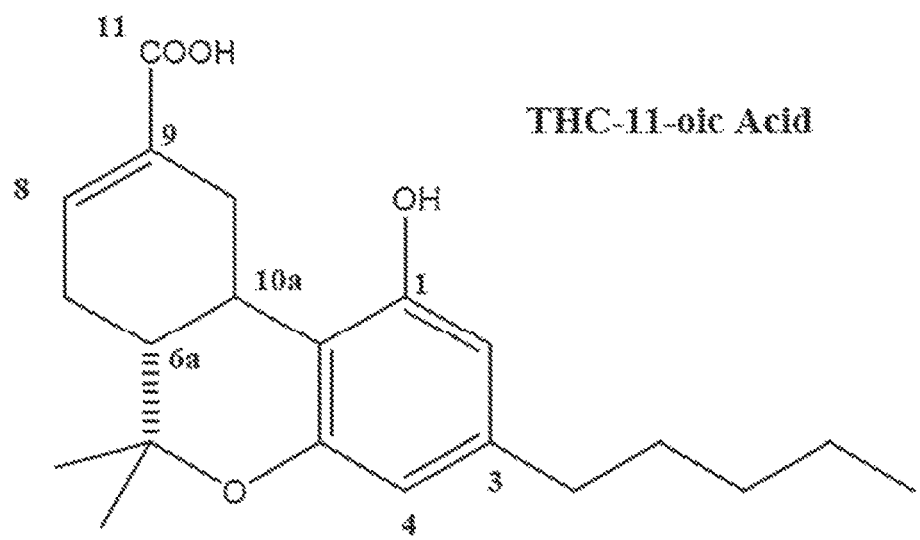
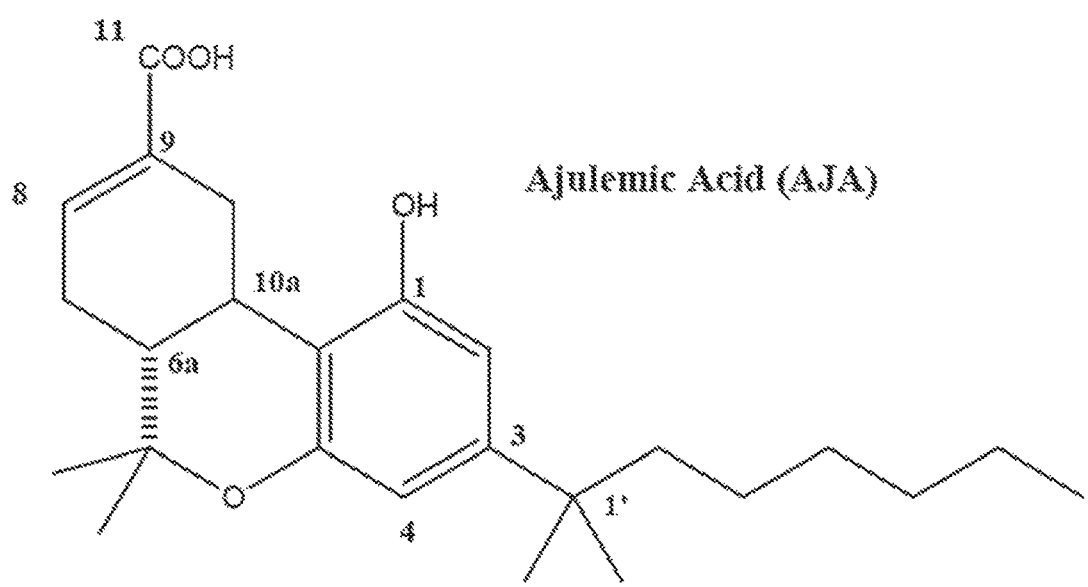

FIGURE 4

|  | AJA(FROM PATENT 5,338,753) | AJA(AMRI) 3306-C-R0-01-49-01 | AJA(NORAC ULTRAPURE) JBA1001A04 |
|---|---|---|---|
| METHOD OF SYNTHESIS | OXIDATION OF ALCOHOL TO CARBOXYLIC ACID | OXIDATION OF METHYL TO CARBOXYLIC ACID | OXIDATION OF METHYL TO CARBOXYLIC ACID |
| MATERIAL APPEARANCE | UNKNOWN | TAN SOLID | WHITE TO TAN SOLID |
| APCI-MS | CONSISTENT WITH STRUCTURE | CONSISTENT WITH STRUCTURE | CONSISTENT WITH STRUCTURE |
| PROTON NMR | CONSISTENT WITH STRUCTURE | CONSISTENT WITH STRUCTURE | CONSISTENT WITH STRUCTURE |
| CARBON NMR | UNKOWN | CONSISTENT WITH STRUCTURE | CONSISTENT WITH STRUCTURE |
| IR SPECTRUM | BROADBAND 3100-3600NM | BROADBAND 2900-3000NM | BROADBAND 2900-3000NM |
| MELTING POINT | 112-114°C | 97-99°C | 97-99°C |
| BINDING AFFINITY | CB1>CB2 (5:1) | CB2>CB1 (13:1) | CB2>CB1 (12:1) |
| PURITY% (HPLC) | UNKOWN | 99.0% | 99.8% |
| TOTAL IMPURITIES | UNKOWN | 0.3% | 0.2% |
| RESIDUAL SOLVENT | UNKOWN | <5000PPM | <300PPM |
| WATER CONTENT | UNKOWN | 1.6% | 1.0% |
| HEAVY METALS | UNKOWN | 15PPM | 21PPM |

FIGURE 8

| Test Name | Specifications | Test Result | | Date Analysis Completed |
|---|---|---|---|---|
| Material Appearance | White to tan solid | Pass (White to Tan Solid) | | 13 June 12 |
| Identity, FTIR | Conforms to Reference Standard | Pass (Conforms to Reference Standard) | | 04 June 12 |
| Identity, $^1$H and $^{13}$C NMR | Conforms to Reference Standard | Pass (Conforms to Reference Standard) | | 31 May 12 |
| Identity, LCMS | Consistent with Structure | Pass [M+1] = 401.17 (Consistent with Structure) | | 31 May 12 |
| Identity, RT by HPLC | Retention Time ± 2% of Reference Standard | Pass (Retention time ± 2% of Reference Standard) | | 14 June 12 |
| Assay, HPLC | 95.0 – 102.0% w/w | 100.2% w/w[1] | | 25 June 12 |
| Purity, HPLC | ≥ 97.0% AUC | 99.8% AUC | | 14 June 12 |
| Related Impurities, HPLC | | | | |
| Individual Related Impurities | ≤ 0.50% AUC each | RRT: 0.82 / 1.05 | Result: 0.06% / 0.14% | 14 June 12 |
| Total Related Impurities | ≤ 3.0% AUC | 0.2% | | |

| Residual Solvents, GC-HS | | Specifications | Test Result | Date |
|---|---|---|---|---|
| | Acetonitrile | ≤ 410 ppm | 69 ppm | 18 June 12 |
| | THF | ≤ 720 ppm | ND | |
| | Toluene | ≤ 890 ppm | ND | |
| | Acetone | ≤ 5000 ppm | 29 ppm | |
| | IPA | ≤ 5000 ppm | 25 ppm | |
| | Heptane | ≤ 5000 ppm | 8 ppm | |
| | MTBE | ≤ 5000 ppm | 164 ppm | |
| | tert-BuOH | ≤ 5000 ppm | ND | |
| Water content, KF | | Report Result | 1.0% | 05 June 12 |
| Residue on Ignition | | Report Result | 0.12% w/w | 31 May 12 |
| Melting Range, DSC | | Report Result | Onset: 92.75 °C Peak: 99.03 °C | 05 June 12 |
| Metals Analysis, ICP-MS | | Report Result | ND for elements listed in USP 35 <231>[2] | 14 June 12 |
| Selenium Content, ICP | | ≤ 50 ppm | 21 ppm | 14 June 12 |

FIGURE 9

| Affinity Constants for Selected Cannabinoids | | | |
|---|---|---|---|
| Ligand | Ki CB2 | Ki CB1 | Ki CB1/Ki CB2 |
| AJA (JBT-101) | 51 (31,82) | 628 (150, 2500) | 12.3 |
| AJA (AMRI) | 43 (22, 84) | 582 (300, 1250) | 13.5 |
| AJA (753 Patent)[3] | 170.5[1] | 32.3[1] | 0.19 |
| WIN-55,212 | 0.3 to 16.2[2] | 1.9 to 123[2] | ND |
| SR144528 | 0.3 to 5.6[2] | 50.3 to >10,000[2] | ND |
| SR141716 | 514 to 13,200[2] | 1.8 to 12.3[2] | ND |

The binding data for the JBT-101 and AMRI preparations represent the means ± (ranges) of 3 to 11 independent experiments. [1]Data taken from Rhee et. al., 1997. [2]Data taken from Pertwee et. al., 2010. *radioligand binding performed as described in the methods using [$^3$H]-CP 55,940. All values are in nM units. [3]U.S. Patent No. 5,338,753.

1. Rhee, M. H.; Vogel, Z.; Barg, J.; Bayewitch, M.; Levy, R.; Hanus, L.; Breuer, A.; Mechoulam, R. *J Med Chem* 1997, *40*, 3228.
2. Pertwee, R. G.; Howlett, A. C.; Abood, M. E.; Alexander, S. P.; Di Marzo, V.; Elphick, M. R.; Greasley, P. J.; Hansen, H. S.; Kunos, G.; Mackie, K.; Mechoulam, R.; Ross, R. A. *Pharmacol Rev* 2010, *62*, 588.

FIGURE 10

Cataleptic Effects in the Mouse[a]

| treatment | dose (mg/kg) | response ± SD |
|---|---|---|
| vehicle[b] | — | 7.7 ± 4.4 |
| 1a | 0.1 | 22.9 ± 10.3* |
| 3a | 0.1 | 5.8 ± 3.4 |
| 3a (AJA) | 1.0 | 12.2 ± 6.0 |
| 6a | 0.25 | 12.3 ± 10.3 |
| 6a | 0.5 | 13.8 ± 7.9 |
| 6a | 1.0 | 10.4 ± 10.6 |
| 6a | 4.0 | 8.7 ± 5.6 |
| $\Delta^6$-THC-7-oic acid | 5.0 | 10.1 ± 6.8 |
| $\Delta^6$-THC-7-oic acid | 0.5 | 10.0 ± 7.5 |
| $\Delta^1$-THC | 40 | 48.9 ± 16* |

[a] The values are expressed as the means of the fraction of time the mice remained immobile ± SD. See the Experimental Section for other details. An asterisk (*) indicates 95% significance by ANOVA; otherwise not statistically significant. [b] Peanut oil (50 μL) given orally.

Antinociceptive Effects[c]

| Dose (mg/kg) | 2a | 1a | 6b | 3c | 6a | 3a |
|---|---|---|---|---|---|---|
| .025 | — | — | — | — | 10.3(5) | 20.8(5) |
| .050 | — | — | — | — | 61.7(5)* | 85.0(5)* |
| 0.10 | — | — | — | — | 49.5(20)* | 68.3(5)*** |
| 0.25 | 30.0(5)* | 44.4(5)* | 10.4(5) | — | 61.5(17)*** | 31.4(5)* |
| 0.50 | 72.5(5)*** | 58.5(5)** | 49.8(10)* | −2.8(6) | 51.7(8)* | 34.0(5) |
| 1.0 | −10.2(5) | 106.1(5)* | 61.4(15)* | — | 14.7(5) | 28.4(5) |
| 2.0 | — | — | 37.5(10) | 42.5(9) | — | — |
| 4.0 | — | — | 3.1(10) | — | — | — |

[c] Values are the percent change in latency. Figures in brackets are the number of mice. *P<0.05; P<0.01; *P<0.001 by a paired t test; otherwise not statistically significant. Under the same conditions indomethacin (10 mg/kg) gave a 51.1% increase in latency and naproxen (40 mg/kg) produced a 64.4% increase.

FIGURE 11

Plasma and brain levels of cannabinoids following systemic administration in rats

|  | CT-3 | | WIN55,212-2 | | Δ⁹-THC | |
|---|---|---|---|---|---|---|
|  | 1 h | 3 h | 1 h | 3 h | 1 h | 3 h |
| Plasma | 1378±120 | 936±75 | 150±17 | 104±22 | 156±19 | 178±25 |
| Brain | 455±103 | 390±15 | 197±27 | 203±40 | 154±13 | 184±33 |
| Brain/plasma ratio | 0.3 | 0.4 | 1.3 | 1.9 | 1.0 | 1.0 |

Concentrations in plasma and brain samples from rats obtained following oral administration of CT-3 (3 mg/kg), or subcutaneous administration of WIN55,212-2 and Δ⁹-THC (10 mg/kg) were measured by HPLC/MS. Data show mean ± SEM from three rats per time point.

Table taken from Dyson et. al., Pain 116: 129-137 (2005).

FIGURE 12

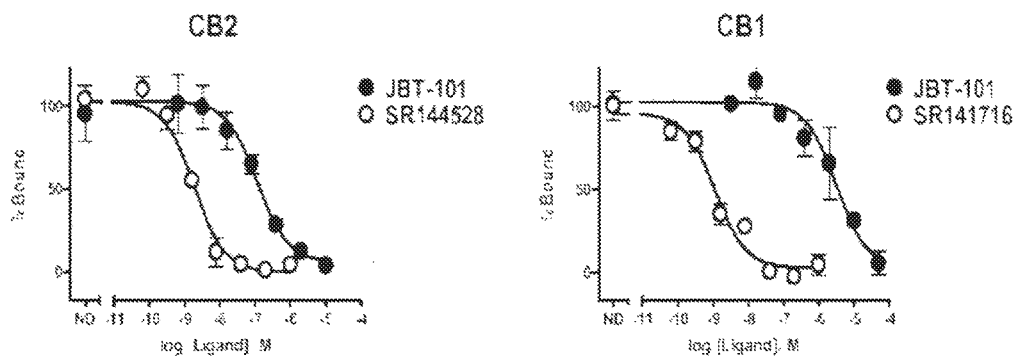

ULTRAPURE TETRAHYDROCANNABINOL-11-OIC ACIDS

CROSS REFERENCE TO RELATED APPLICATIONS

This application claims priority to U.S. Non-Provisional application Ser. No. 15/220,127 (filed on Jul. 26, 2016), Ser. No. 15/347,059 (filed on Nov. 9, 2016), and Ser. No. 15/347,104 (filed on Nov. 9, 2016), the disclosure of each of which is incorporated herein by reference in their entirety.

FIELD OF THE INVENTION

This invention is in the field of medicinal chemistry and relates to ultrapure tetrahydrocannabinol-11-oic acids compounds, pharmaceutical compositions and synthesis thereof. The invention also relates to methods of using the compounds and pharmaceutical compositions of this invention to treat and/or prevent various conditions such as inflammation, pain and fibrosis.

BACKGROUND OF THE INVENTION

Tetrahydrocannabinol (THC) is the major psychoactive constituent of marijuana. In addition to mood-altering effects, THC has been reported to exhibit other activities, some of which may have therapeutic value, including analgesic, anti-inflammatory and anti-emetic properties. The potential therapeutic value of THC has led to a search for related compounds which minimize the psychoactive effects, while retaining the activities of potential medicinal value.

For example, (6aR,10aR)-3-(1',1'-dimethylheptyl)-Δ8-tetrahydro-cannabinol-9-carboxylic acid (IUPAC name), also known as ajulemic acid (AJA) is a candidate for the treatment of pain and inflammation either alone or in combination with other agents.

The current body of knowledge of cannabinoid research in pain and inflammation suggests that cannabinoid receptors CB1 and CB2 play an important role in the initiation and maintenance of post-synaptic signaling and immune mechanisms related to nociception, sensitization, pain signal transmission and pain processing. Previously, impure preparations of ajulemic acid have been shown to have affinity for both CB1 and CB2 receptors, with more affinity for the CB1 receptor (14). The present invention, for the first time, provides a highly purified form of ajulemic acid which exhibits a higher affinity for the CB2 receptor than the CB1 receptor.

The ultrapure ajulemic acid can be used to treat fibrotic diseases such as scleroderma, systemic sclerosis, scleroderma-like disorders, sine scleroderma, liver cirrhosis, interstitial pulmonary fibrosis, idiopathic pulmonary fibrosis, Dupuytren's contracture, keloids, chronic kidney disease, chronic graft rejection, fibrosis of organs such as liver, esophagus, heart, lung, intestines, etc., and other scarring/wound healing abnormalities, post-operative adhesions, and reactive fibrosis as well as, inflammatory diseases such as lupus, multiple sclerosis, rheumatoid arthritis, dermatomyositis, Marfan's syndrome, psoriasis, Type 1 diabetes, diabetes, cancer, asthma, atopic dermatitis, autoimmune thyroid disorders, ulcerative colitis, Crohn's disease, Parkinson's disease, Alzheimer's disease, HIV infection, stroke and ischemia, where activation of the CB2 receptor plays a role in the pathophysiology of the disease.

SUMMARY

The present invention provides for a composition comprising ultrapure ajulemic acid, wherein the ajulemic acid has an affinity for the CB2 receptor greater than its affinity for the CB1 receptor. In some embodiments, ultrapure ajulemic acid has an affinity for the CB2 receptor ranging from about 2 times to about 100 times, from about 5 times to 50 times, from about 15 times to 50 times, from about 10 times to about 40 times, or from about 20 times to about 40 times greater than its affinity for the CB1 receptor. The present invention provides for a composition comprising ajulemic acid, wherein the ajulemic acid has a $K_i$ for the CB1 receptor greater than its $K_i$ for the CB2 receptor. In some embodiments, ajulemic acid has a $K_i$ for the CB1 receptor ranging from about 2 times to about 100 times, from about 5 times to 50 times, from about 15 times to 50 times, from about 10 times to about 40 times, or from about 20 times to about 40 times greater than its $K_i$ for the CB2 receptor. The ajulemic acid in the present composition may have purity greater than about 97%, greater than about 98%, or greater than about 99%.

The present invention also provides for a composition comprising ajulemic acid, wherein the ajulemic acid has a purity greater than about 97%, greater than about 98%, or greater than about 99%.

The present invention provides for a composition comprising ajulemic acid, wherein the ajulemic acid has less than about 1% (w/w), less than about 0.5% (w/w), less than about 0.3% (w/w), less than about 0.2% (w/w), less than about 0.1% (w/w), or less than about 0.05% (w/w) of 11-hydroxy-(6aR,10aR)-3-(1',1'-dimethylheptyl)-6,8-tetrahydrocannabinol (HU-210) or other highly CB1 active compounds.

The ajulemic acid in the present composition may have an affinity for the CB2 receptor greater than its affinity for the CB1 receptor. In some embodiments, ajulemic acid has an affinity for the CB2 receptor ranging from about five times to fifty times, from about ten times to fifty times, from about twenty times to about forty times greater than its affinity for the CB1 receptor.

The present invention further provides for a method of treating a subject with fibrotic disease comprising administering a therapeutically effective amount of ajulemic acid to the subject, wherein the ajulemic acid has an affinity for the CB2 receptor greater than its affinity for the CB1 receptor. In some embodiments, ajulemic acid has an affinity for the CB2 receptor ranging from about 2 times to about 100 times, from about 5 times to 50 times, from about 15 times to 50 times, from about 10 times to about 40 times, or from about 20 times to about 40 times greater than its affinity for the CB1 receptor. The fibrotic disease may be dermal fibrosis, lung fibrosis, liver fibrosis, kidney fibrosis, heart fibrosis or any other organ fibrosis. The fibrotic disease may be scleroderma, systemic sclerosis, scleroderma-like disorders, sine scleroderma, liver cirrhosis, interstitial pulmonary fibrosis, idiopathic pulmonary fibrosis, Dupuytren's contracture, keloids, cystic fibrosis, chronic kidney disease, chronic graft rejection, or other scarring/wound healing abnormalities, post-operative adhesions, and reactive fibrosis.

The ajulemic acid may be administered orally, intravenously, topically, ophthalmically, interstitially, by inhalation or via an implant or patch.

The present invention provides for a method of reducing pain in a subject comprising, administering a therapeutically effective amount of ultrapure ajulemic acid. The ajulemic acid may have an affinity for the CB2 receptor greater than the affinity for the CB1 receptor. In some embodiments, ajulemic acid has an affinity for the CB2 receptor ranging from about 2 times to about 100 times, from about 5 times to 50 times, from about 15 times to 50 times, from about 10 times to about 40 times, or from about 20 times to about 40 times greater than its affinity for the CB1 receptor. The reduction of pain may be measured along at least one pain scale. For example, the pain may be reduced by at least about 1 point, at least about 2 points, at least about 3 points, at least about 4 points, at least about 5 points, at least about 6 points, at least about 7 points, or at least about 8 points on an 11-point pain scale.

The present invention also provides for a method of reducing inflammation in a subject comprising, administering a therapeutically effective amount of ultrapure ajulemic acid. The ajulemic acid may have an affinity for the CB2 receptor greater than the affinity for the CB1 receptor. In some embodiments, ajulemic acid has an affinity for the CB2 receptor ranging from about 2 times to about 100 times, from about 5 times to 50 times, from about 15 times to 50 times, from about 10 times to about 40 times, or from about 20 times to about 40 times greater than its affinity for the CB1 receptor. The reduction of inflammation may be measured by at least one inflammation assay.

DESCRIPTION OF THE FIGURES

FIG. 1 shows the structure of ajulemic acid ((6aR,10aR)-3-(1',1'-dimethylheptyl)-Δ8-tetrahydrocannabinol-9-carboxylic acid) and the naturally occurring pentyl side chain analog, (6aR,10aR)-Δ8-tetrahydrocannabinol-9-carboxylic acid.

FIG. 4 shows a comparison of the properties of batches of AJA as described in U.S. Pat. No. 5,338,753 and ultrapure AJA made with 5-(1',1'-dimethylheptyl)-resorcinol (DMHR)—lot JBA1001A04.

FIG. 8 shows an analysis of ultrapure AJA showing 99.8% purity.

FIG. 9 shows affinity constants for selected cannabinoids. The ultrapure AJA shows a major difference between the $K_i$ for CB1 and CB2 receptors.

FIG. 10 shows the cataleptic and antinociceptive effects of AJA from Burstein, S. H. et al. (1992) Synthetic nonpsychotropic cannabinoids with potent antiinflammatory, analgesic, and leukocyte antiadhesion activities, J Med Chem 35(17), 3135-3141.

FIG. 11 shows plasma and brain levels of cannabinoids following systemic administration in rats as described in Dyson et al. [3].

FIG. 12 shows representative binding curves of selected cannabinoids for CB2 and CB1.

DETAILED DESCRIPTION OF THE INVENTION

THC Derivatives

Figure 2:
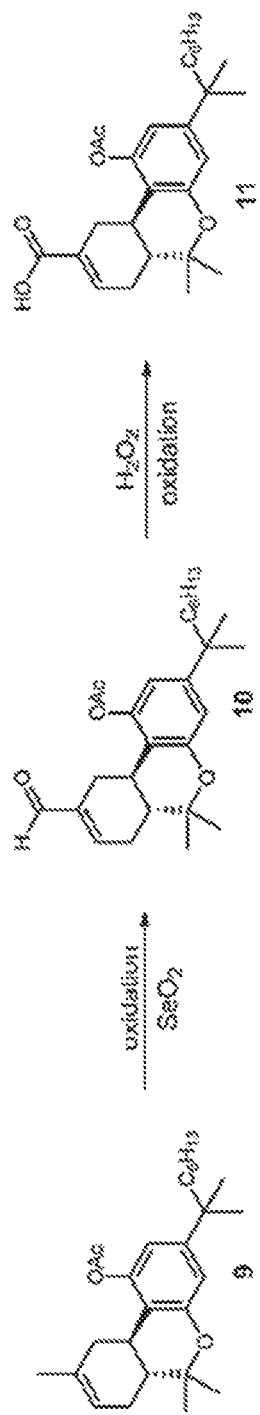
FIG. 2 shows some critical steps for the synthesis of ultrapure ajulemic acid synthesis.

Tetrahydrocannabinol (THC) is the major psychoactive constituent of marijuana. In addition to mood-altering effects, THC has been reported to exhibit other activities, some of which may have therapeutic value, including analgesic, anti-inflammatory and anti-emetic properties. The potential therapeutic value of THC has led to a search for related compounds which minimize the psychoactive effects, while retaining the activities of potential medicinal value.

For example, (6aR,10aR)-3-(1',1'-dimethylheptyl)-Δ8-tetrahydro-cannabinol-9-carboxylic acid, also known as ajulemic acid, may be used for the treatment of pain and inflammation either alone or in combination with other agents.

The current body of knowledge of cannabinoid research in pain and inflammation suggests that CB1 and CB2 receptors play an important role in the initiation and maintenance of post-synaptic signaling and immune mechanisms related to nociception, sensitization, pain signal transmission and pain processing. [C. Voscopoulos and M. Lema, Br.

J. Anaesth. (2010) 105 (suppl 1): i69-i85.]. Previously, earlier preparations of ajulemic acid have been shown to have affinity for both CB1 and CB2 receptors, with higher affinity for the CB1 receptor. The present invention, for the first time, provides for a purified form of ajulemic acid with higher affinity for the CB2 receptor vs the CB1 receptor. The purified form of ajulemic acid is also referred to as ultrapure ajulemic acid.

In various embodiments, the degree of purity of the ajulemic acid is greater than about 95% (w/w), greater than about 96% (w/w), greater than about 97% (w/w), greater than about 98% (w/w), greater than about 99% v, greater than about 99.1% (w/w), greater than about 99.2% (w/w), greater than about 99.3% (w/w), greater than about 99.4% (w/w), greater than about 99.5% (w/w) or greater than about 99.9% (w/w). The degree of purity may be assessed by a variety of different methods as described further below.

The affinity of the purified form of ajulemic acid for the CB2 receptor can range from about five-fold to about ten-fold greater than the affinity for the CB1 receptor, but affinity ranges from about 5×-50×, 7×-10×, 8×-15×, 10×-20×, 15×-30×, 25×-50×, 40-75× and 50×-100× are also encompassed by the invention (ranges represent ratios of affinity of ajulemic acid for the CB2 receptor versus the CB1 receptor).

In one embodiment, the present compound has the structure shown in Formula I. The present compounds may have a purity of greater than about 97%, about 98%, about 99%, about 99.1%, about 99.2%, about 99.3%, about 99.4%, about 99.5% or about 99.9%. The present compounds may contain less than 0.1% (w/w) of 11-hydroxy-(6aR,10aR)-3-(1',1'-dimethylheptyl)-Δ8-tetrahydrocannabinol (HU-210) or other highly CB1 active compounds. The purified form of the present compounds may also be referred to as an ultrapure form. Also encompassed by the present invention are the pharmaceutically acceptable salts, esters, or solvate of the compound in Formula I.

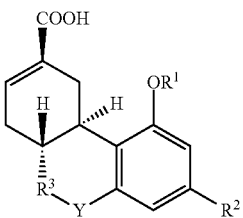

Formula I where $R_1$ is hydrogen, $COCH_3$ or $COCH_2CH_3$; $R_2$ is a branched C5-C12 alkyl group which may optionally have a terminal aromatic ring, or optionally a branched $OCHCH_3(CH_2)_m$ alkyl group which may have a terminal aromatic ring and where m is 0 to 7; $R_3$ is hydrogen, a C1-8 alkyl or a C1-8 alkanol group; and Y is either zero, i.e. absent, or a bridging group of NH or oxygen, (provided that where Y is oxygen and $R_2$ is a branched C5-C12 alkyl, $R_3$ is not $CHCH_3$).

Preparation of Ultrapure Ajulemic Acid

The present invention provides for a process of preparing a purified form of ajulemic acid. The process may contain the following steps: (a) reacting Para-mentha-2,8-dienl-ol (PMD) and 5-(1,1-dimethylheptyl) resorcinol (DMHR) to form (6aR,10aR)-3-(1',1'-dimethylheptyl)-Δ8-tetrahydrocannabinol (Compound 8); (b) acetylating Compound 8 to form (6aR,10aR)-3-(1',1'-dimethylheptyl)-Δ8-tetrahydrocannabinol acetate (Compound 9); (c) oxidizing Compound 9 to form 11-oxo-(6aR,10aR)-3-(1',1'-dimethylheptyl)-Δ8-tetrahydrocannabinol acetate (Compound 10); (d) oxidizing Compound 10 to form (6aR,10aR)-3-(1',1'-dimethylheptyl)-Δ8-tetrahydrocannabinol-9-carboxylic acid acetate (Compound 11) using hydrogen peroxide, wherein the molar ratio of hydrogen peroxide to Compound 9 ranges from about 2:1 to about 7:1; (e) hydrolyzing Compound 11 to produce crude ajulemic acid; (f) acetylating crude ajulemic acid to form Compound 11; and, (g) hydrolyzing Compound 11 to form the purified form of ajulemic acid.

In step (d), the molar ratio of hydrogen peroxide to Compound 9 may also range from about 2:1 to about 6:1, from about 2:1 to about 5:1, from about 2:1 to about 4:1, about 2:1, about 2.5:1, about 3:1, about 3.5:1, or about 4:1. In step (a), the molar ratio of PMD to DMHR may range from about 1:1 to about 3:1, from about 1:1 to about 2:1, from about 1:1 to about 1.1:1, about 1.1:1, or about 1.2:1. Step (a) may be carried out at about 50° C. to about 120° C., about 60° C. to about 110° C., about 70° C. to about 100° C., about 75° C. to about 90° C., about 70° C. to about 80° C., about 70° C., about 75° C., or about 80° C. The purified ajulemic acid may have a purity greater than about 95% (w/w), greater than about 96% (w/w), greater than about 97% (w/w), greater than about 98% (w/w), greater than about 99% v, greater than about 99.1% (w/w), greater than about 99.2% (w/w), greater than about 99.3% (w/w), greater than about 99.4% (w/w), greater than about 99.5% (w/w) or greater than about 99.9% (w/w).

In certain embodiments, the compounds of the invention contain one or more chiral centers. The term "purity" can also encompass chiral purity. The purity of a stereoisomer of ajulemic acid refers to chemical purity and/or chiral purity of the stereoisomer. For example, the purity of ajulemic acid can include both the chemical purity and the chiral purity of ajulemic acid. The chiral purity of a stereoisomer of ajulemic acid may be greater than about 98.5% (w/w), greater than about greater than about 95% (w/w), greater than about 96% (w/w), greater than about 97% (w/w), greater than about 98% (w/w), greater than about 99% v, greater than about 99.1% (w/w), greater than about 99.2% (w/w), greater than about 99.3% (w/w), greater than about 99.4% (w/w), greater than about 99.5% (w/w) or greater than about 99.9% (w/w).

The purity of the present compounds may be assayed by gas chromatography (GC) or high pressure liquid chromatography (HPLC). Other techniques for assaying the purity of ajulemic acid and for determining the presence of impurities include, but are not limited to, nuclear magnetic resonance (NMR) spectroscopy, mass spectrometry (MS), GC-MS, infrared spectroscopy (IR), thin layer chromatography (TLC), and differential scanning calorimetry. Chiral purity can be assessed by chiral GC or measurement of optical rotation.

The purified form of ajulemic acid may be stable after storage. For example, after storage at about 5° C. for at least 3 months, the present composition may contain greater than about 98.5% (w/w), greater than about 99% (w/w), greater than about 99.5% (w/w), or greater than about 99.9% (w/w) ajulemic acid. After storage at 25° C. and 60% relative humidity for at least 3 months, the present composition can contain greater than about 98.5% (w/w), greater than about 99% (w/w), greater than about 99.5% (w/w), or greater than about 99.9% (w/w) ajulemic acid.

Several embodiments of the process are described below. They are presented for the purposes of illustration only and are not limiting the invention.

Purification

A. Optimization of Allylic Oxidation Applied to Synthesis of Ajulemic Acid

The allylic oxidation of Compound 9 containing a methyl at the 11 position with selenium dioxide followed by hydrogen peroxide provides a way of synthesizing Ajulemic acid to completion without yielding incompletely oxidized intermediates such as the alcohol at the 11 position which gives the highly CB1 active HU-210. Initial laboratory experiments using 8 equivalents of hydrogen peroxide, relative to Compound 9, indicated that an adequate conversion was achieved in 4-6 hr[4], see FIG. 2.

Because oxidation reactions are potentially hazardous especially when conducted at a large scale, safety assessments are performed. The number of equivalents of hydrogen peroxide was varied from 2, 2.5, 3 and 4 equivalents[5]. The thermal onset temperature with these reduced equivalents of hydrogen peroxide did not change from the onset temperature of 55° C. observed with 8 equivalents, but the maximum self heat rate when the reduced equivalents of hydrogen peroxide were used was just 7° C./min which is significantly reduced from the previously observed 1000° C./min measured when 8 equivalents of hydrogen peroxide were used. In the case when 2 equivalents of hydrogen peroxide were used, no thermal event was observed, however reaction completion was not achieved, with a 74.1% conversion of the aldehyde to acid being achieved after 45 h which did not meet the specification of ≤10.0% of the aldehyde. For the 2.5, 3 and 4 equivalents, reaction completion was achieved, however, with these numbers of equivalents of hydrogen peroxide, there was still a potential for a runaway reaction.

Therefore calculations were performed, assuming the use of 4 equivalents of hydrogen peroxide, to determine the rate of addition of chilled water and the volume required to quench the reaction in the event of a thermal runaway. An adequate rate of addition and volume of chilled water was determined for controlling a thermal runaway at a rate of 7° C./min, and protocols implemented for running a 400 g non-GMP batch using 3 equivalents of hydrogen peroxide, with pre-chilled water being available in the event of a thermal runaway. No uncontrollable thermal event was observed during the execution of this step in the production run. An improved yield was also observed over the 3 steps with an increase from 16% to 21% yield.

There are several advantages over prior art. While the reagents used in the synthesis have not changed, it has been demonstrated that the prior art, using 8 equivalents of hydrogen peroxide[1], was operating too close to a potential catastrophic event. By conducting safety evaluations and looking at reduced equivalents of hydrogen peroxide, a safely scalable process for the allylic oxidation reaction used in the synthesis of ultrapure Ajulemic Acid has been defined, while also improving the yield from 16% to 21%.

B. Improved Synthesis of Ajulemic Acid from DMHR and PMD

Ultrapure DMHR (5-(1,1-dimethylheptyl)resorcinol)) may be purchased from Norac Pharma (Azusa, Calif.).

Improved Synthetic Procedure and Safety

Figure 3:
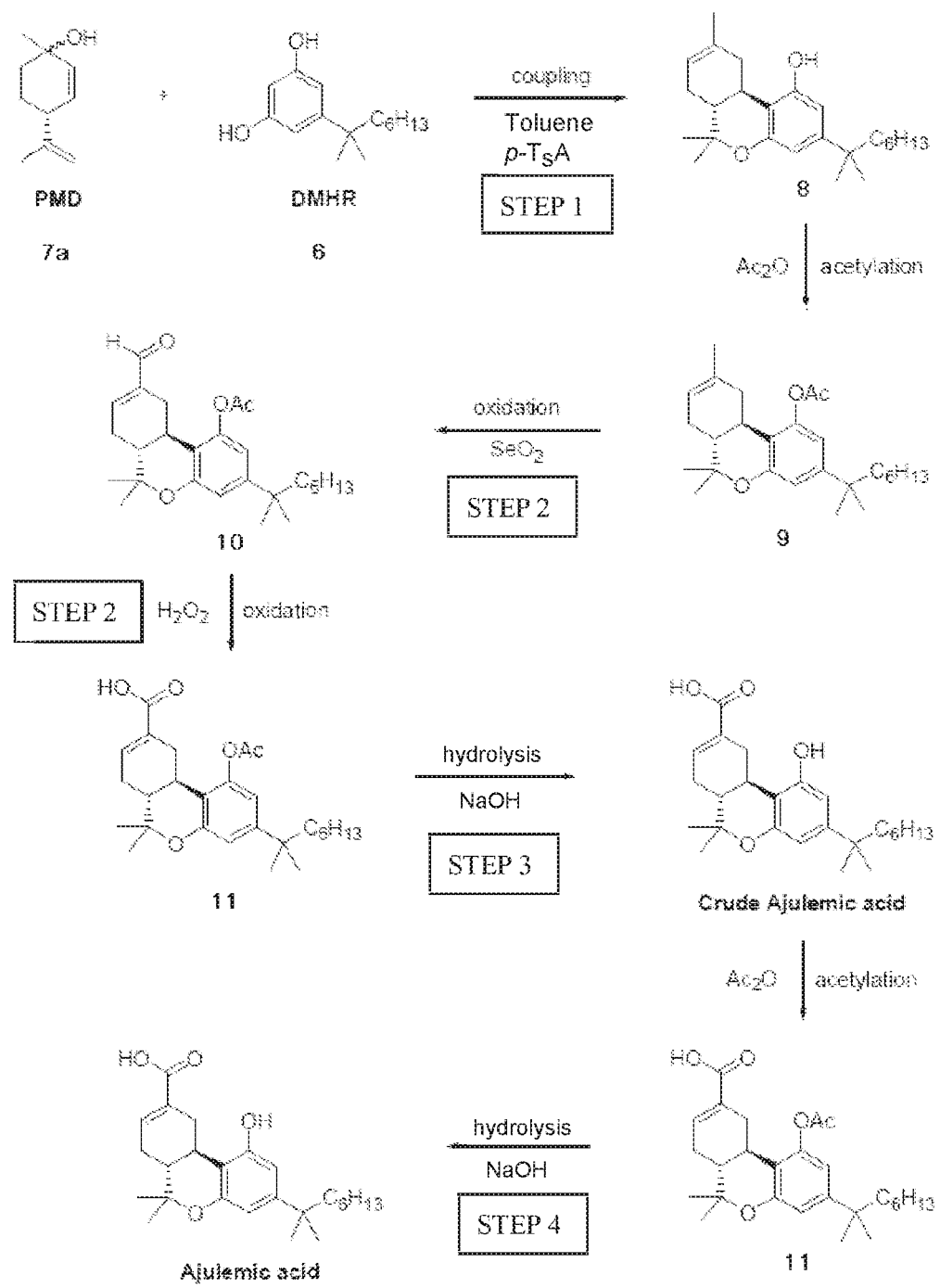
FIG. 3 shows a scheme for synthesis of ultrapure Ajulemic Acid (AJA).
Figure 5A:
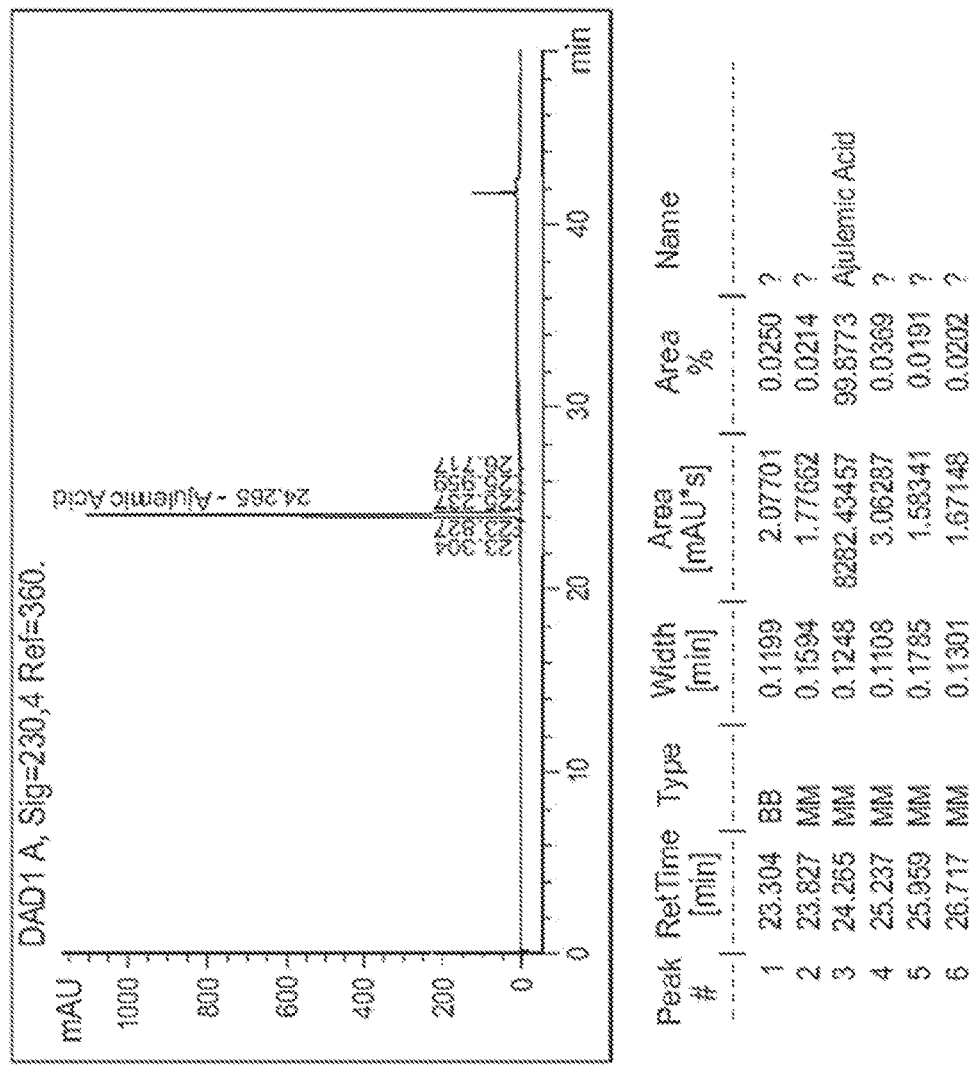
FIGS. 5A and 5B show an LC-MS analysis of AJA made with ultrapure 5-(1',1'-dimethylheptyl)-resorcinol (DMHR).
Figure 5B:
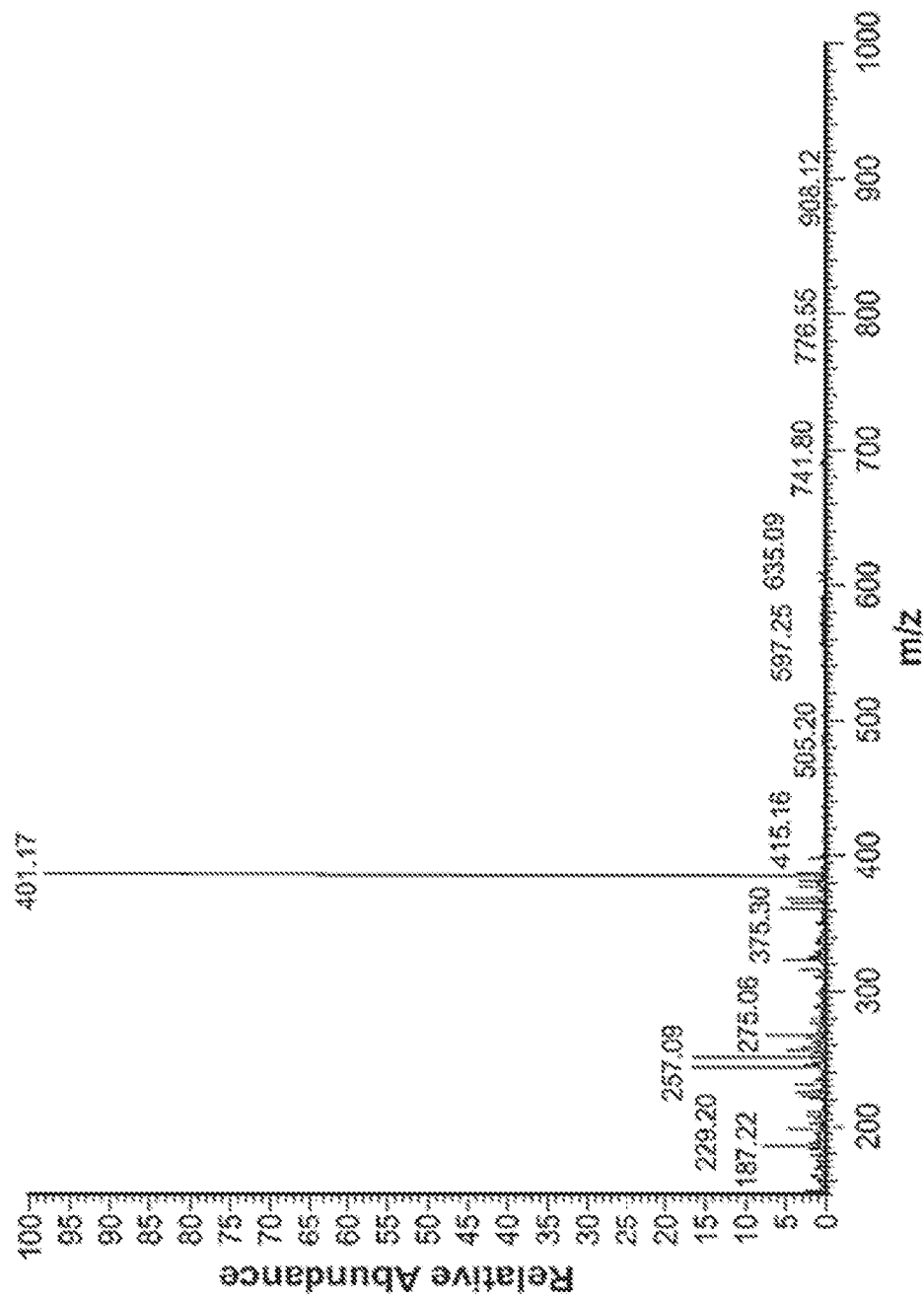
Figure 6:
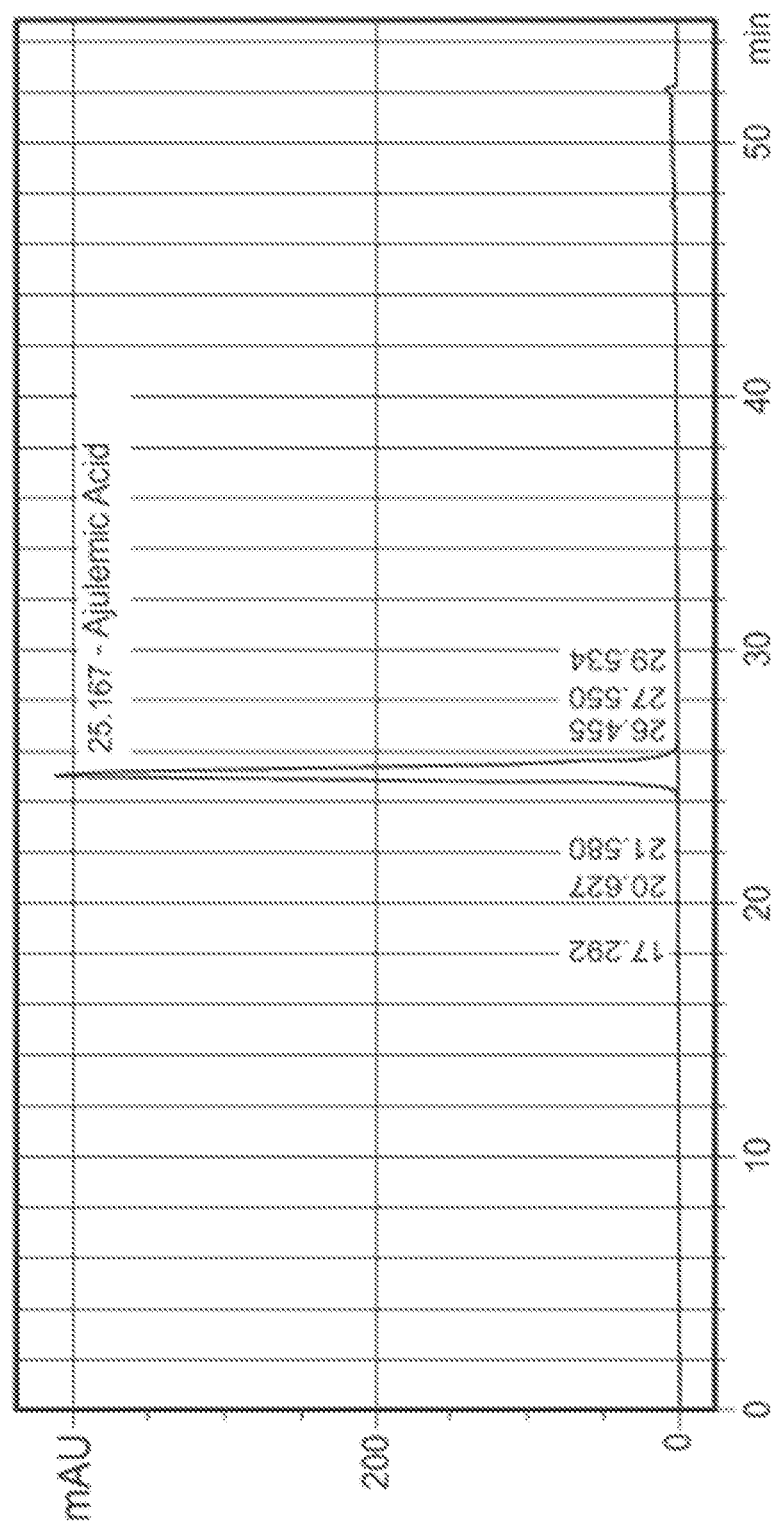
FIG. 6 shows an HPLC analysis of synthesized ultrapure AJA.
Figure 7:
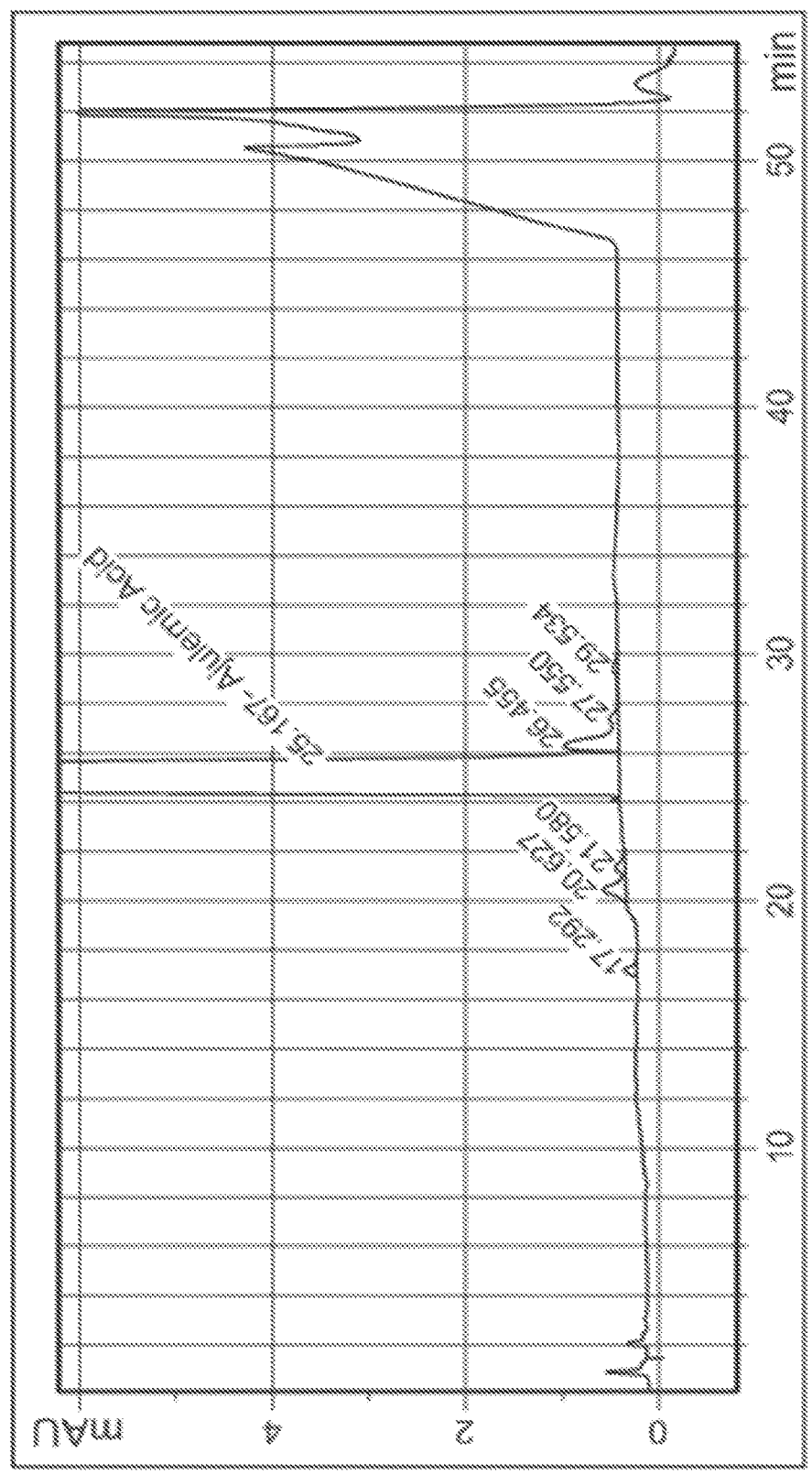
FIG. 7 shows a magnified image of an HPLC analysis of synthesized ultrapure AJA.

Step 1 Preparation of (6aR,10aR)-3-(1',1'-dimethylheptyl)-Δ8-tetrahydrocannabinol Firstly, the amount of PMD (7a in FIG. 3) used in the reaction was reduced from 1.25 equivalents to 1.1 equivalents, because the 0.1 equivalents excess of PMD was sufficient to react with all of the DMHR (6 in FIG. 3).

The previous procedure describes heating the batch to reflux (~110° C.) for 3 h. Although effective in azeotropically removing water and meeting the specification of ≤2.0% (AUC) cannabidiol, this procedure induced Compound 1 decomposition and DMHR regeneration upon prolonged heating. To avoid byproduct formation, the reaction was conducted at 75° C., the same temperature as the subsequent acetylation reaction, and was stable over 24 h with no effects on reaction time. In order to azeotropically remove water, the reaction was placed under partial vacuum. A Dean-Stark trap was used to collect the water and the endpoint was redefined as the point in which no more water was being collected in the trap.

Lastly, the crystallization conditions were re-examined. Solubility studies revealed that the most effective isopropyl alcohol (IPA): water ratio to improve yield was in the range of 3:1 to 5:1 IPA: water. This contrasted the previous procedure, which employed a 5.33:1 ratio. After experimentation with different ratios, 8:2 IPA: water was used as the solvent ratio for crystallization. Also, crystal size was improved by slowing the stirring rate, which kept the larger crystals intact.

Seed crystals were no longer required for crystallization because the Acetylated PMD/DMHR coupled product consistently crystallizes following the procedure described.

Step 2 Preparation of (6aR,10aR)-3-(1',1'-dimethylheptyl)-Δ8-tetrahydrocannabinol-9-carboxylic acid acetate The previous procedure used 3 equivalents of hydrogen peroxide for the oxidation reaction. While this was much safer than the 8 equivalents used in another previous procedure, there was still a possibility of a thermal runaway. Accordingly, 2 equivalents of hydrogen peroxide was evaluated, because previous safety studies showed that 2 equivalents of hydrogen peroxide drastically reduced the risk of thermal runaway. After 48 h, the reaction did not meet the specification of <10% (AUC) of unreacted aldehyde. Regardless, the reaction was taken through to Crude Ajulemic acid (6.2% yield, 96.8% (AUC) purity). Even though the purity was comparable, the yield was significantly lower than the reaction with 3 equivalents of hydrogen peroxide. 3 equivalents of hydrogen peroxide was used and thus close technical supervision of this step during production can ensure good temperature control. Also, as previously done for the 400 g non-GMP batch, chilled water was present as a quench option in the event of an uncontrolled exothermic reaction.

Toluene was previously used as an extraction solvent after the hydrogen peroxide oxidation. The procedure then required evaporating the mixture to dryness and adding heptane. Since evaporation to dryness is not easily scalable and a solvent swap from toluene to heptane is not efficiently feasible, other solvents were evaluated as possible extraction solvents. Firstly, heptane was assessed. Although heptane successfully extracted the product into the organic layer, the phase split was slow and there were three layers. On the second attempt, no extraction solvent was used and it was observed that quenching the hydrogen peroxide reaction with 20 wt % sodium thiosulfate led to two phases. Thus, the aqueous layer could be removed without additional organic solvents.

During the synthetic process development, the phase split following the hydrolysis was problematic because of the formation of 3 layers, the high viscosity of the middle layer, and the dark color of all the phases. MTBE was evaluated as a possible extraction solvent instead of heptane. Although the MTBE extraction, led to a quick phase split into 2 layers—a dark brown organic layer and a transparent red aqueous layer, HPLC analysis revealed that the product and all of the impurities remained in the organic layer. Heptane was then re-evaluated as the extraction solvent. As observed in the 400 g batch production, the reaction mixture separated into 3 dark layers; however the middle oily layer was much more mobile (believed to be due to THF being present). HPLC analysis showed that the top organic layer contained impurities and no product while the two bottom layers contained mostly product with trace impurities. Although the phase split was still hard to visualize due to the dark color, the heptane extraction was able to separate the product from the impurities.

The subsequent acidification and extraction steps were performed at ambient temperatures instead of 45-55° C. These conditions reduced the risk of hydrolyzing MTBE to produce chloromethane and tert-butanol.

The next step was to filter the batch through Celite to break up emulsions. Because the filtration was noticeably slow, the aqueous layer was removed prior to filtration. The solvent swap from MTBE to acetonitrile was successful and seed crystals were no longer required for crystallization because the Crude Ajulemic acid consistently crystallizes following the procedure described.

Step 3 Preparation of Crude Ajulemic Acid

In order to avoid a difficult solvent swap from toluene to heptane, the acetylation reaction was completed in heptane at 45-55° C. The change was successful on a small scale, but the reaction mixture solidified after ~0.5 equivalents of pyridine was charged to the reactor at a 14.5 g scale. To try to recover the Ajulemic acid, MTBE was added to solubilize the precipitate and HCl was used to remove the pyridine. This attempt was unsuccessful, because the solids precipitated out while evaporating the solvent on the rotary evaporator. NMR analysis revealed that the precipitate was an Ajulemic acid-pyridine partial salt. Several experiments were completed in order to determine the cause of the salt formation. Firstly, the same reaction was performed on a smaller scale (~2.5 g). Pyridine (0.5 equivalents) was slowly added to the mixture. Once again, the reaction solidified. This, however, was remedied upon adding the full 2.1 equivalents of pyridine. The reaction was then performed at 25° C. and 75° C., again adding 0.5 equivalents before adding the full amount of pyridine. In both cases, the salt precipitated but solubilized once all of the pyridine was added. Since a larger batch size will require slower additions, this procedure was deemed un-scalable.

Accordingly, crude Ajulemic acid dissolved in heptane (6 equivalents) was added to a reactor containing the full 2.1 equivalents of pyridine dissolved in heptane (2 equivalents). This avoided the formation of a partial salt because pyridine was always in excess. This also increased the reaction volume to 10 equivalents heptane (2 extra equivalents was used to wash the reactor), which improved mobility during crystallization.

Step 4 Preparation of Ultrapure Ajulemic Acid

Similar changes were made in this step as in the Step 2 work-up as the same reaction was being performed. The acidification of the reaction mixture was done at ambient temperature to avoid MTBE hydrolysis and an extra water wash was added to avoid oven corrosion.

The main issue with Step 4 was the drying time. It required 9 days to reach the specification of ≤410 ppm acetonitrile for the previous 400 g non-GMP campaign batch. Thus, crystallization from IPA/water was evaluated. A solubility study showed that Ajulemic acid in a 1:1 IPA/water mixture had a similar solubility to Ajulemic acid in a 3:1 acetonitrile/water mixture. Although Ajulemic acid was successfully isolated from IPA/water, the drying time did not improve, requiring >7 days to reach the specification of ≤5000 ppm IPA on a 2.5 g scale. The amount of IPA remaining in the product did not correlate with the LOD, suggesting that water played a key role in drying time. Therefore, crystallization from pure acetonitrile was evaluated on a 19.5 g scale. This produced a much shorter drying time with no detectable amount of acetonitrile at 81 h.

A use-test of ultrapure DMHR (purity of 99.4% (AUC)) was successfully taken through to Ajulemic Acid. The purity of the Ajulemic acid was 99.9% (AUC) with no single peak≥0.04%.

C. The Synthesis of Ajulemic Acid from Ultrapure DMHR and PMD (Large Scale)

Step 1

To a 200-gallon reactor were charged ultrapure DMHR (20.0 kg, 1 equiv.), PTSA (3.40 kg, 0.2 equiv.) and toluene (102.3 kg, 5 vol. equiv.). To this was added PMD (14.18 kg, 1.1 equiv.) over 38 min, followed by a toluene rinse (17.4 kg, 1 vol. equiv.) while maintaining the batch temperature at 15-30° C. The batch was heated to 70-80° C. under partial vacuum, and a Dean-Stark trap filled with toluene was used to remove water by azeotropic distillation with toluene while maintaining a constant volume of toluene. The reaction was determined complete after 2 h by HPLC, detecting no cannabidiol and obtaining a Δ8:Δ9 ratio of 106:1 (specification was <2.0% (AUC) cannabidiol and Δ8:Δ9 ratio≥4:1). The batch was held overnight at 25° C. and atmospheric pressure.

The batch was reheated to 70-80° C., and pyridine (10.70 kg, 1.6 equiv.) and acetic anhydride (13.80 kg, 1.6 equiv.) were each added over ~30 min while maintaining the batch temperature at 70-80° C. After 2 h the batch was sampled and passed the specification of ≤2.0% (AUC) of Compound 1 with 0.4% (AUC) Compound 1 detected. Water (160.0 kg, 8 equiv.) was added and the batch was adjusted to 50-60° C. The lower aqueous layer was removed and the batch was further washed with water (40 kg, 2.0 equiv.) at 50-60° C. The reaction mixture was transferred from the 200-gallon reactor to the 250-liter reactor.

Toluene (100 L, 5 vol. equiv.) was distilled off and IPA (78.6 kg, 8 vol. equiv.) was added. This was repeated two more times before the sample was tested and passed the specification of ≤2.0% (AUC) of toluene. The batch was held at 20-30° C. overnight. After IPA (31.4 kg, 2 vol. equiv.) addition, the batch was reheated to 45-55° C., water (40.0 kg, 2 vol. equiv.) was added, and the temperature was maintained for an additional ~1 h before cooling to 25±2° C. at ~10° C./hour. The batch was held at this temperature for over 16 h then cooled to 0-5° C. at 10° C./hour and held for another 2 h 10 min. The slurry contained large particles that would not flow through the bottom outlet valve. Therefore, the product was dissolved back into solution by heating the reactor to 55° C. The batch was cooled to 35° C., held at this temperature overnight, and filtered to yield a 1st crop. The filtrate was then cycled back into the reactor, cooled down to 5° C. and further product was isolated as 2nd crop. Both crops were washed with 20% water in IPA solution (~36 L used to wash 1st crop and ~24 L for 2nd crop). The two crops were then dried under vacuum at 122° F. (50±5° C.). The product was offloaded and gave a total actual weight of 25.76 kg of Compound 2—The 1st crop yielded an actual weight of 14.50 kg (97.0% (AUC) purity) and the 2nd crop yielded an actual weight of 11.26 kg (93.3% (AUC) purity).

Step 2

To a 200-gallon reactor was charged Compound 2 (25.76 kg, 1 equiv.), selenium dioxide (8.66 kg, 1.25 equiv.), tetrahydrofuran (98.5 kg, 4.3 vol. equiv.) and water (5.2 kg, 0.2 equiv.). The reactor was heated and maintained at 55-65°

C. After 20.5 h, the reaction was deemed complete by HPLC, passing the specification of ≤2.0% (AUC) Compound 2 with 1.8% (AUC) residual Compound 2. The batch was cooled to 0-10° C. over ~3 h. While maintaining the batch temperature<25° C., 35 wt % hydrogen peroxide (18.21 kg, 3 equiv.) was added. The batch temperature was then adjusted to 10-25° C. and held at this temperature until the reaction met the specifications of ≤10.0% (AUC) of Compound 10 by HPLC. At ~16 h, the reaction was deemed complete (1.7% (AUC) residual Compound 10) and was slowly quenched with 20 wt % sodium thiosulfate solution (98.8 kg, 2 equiv.) while maintaining the batch temperature<35° C. After 2 h 13 min, there was no trace of peroxide. The batch was filtered through a pad of Celite and the Celite cake was washed with 22.9 kg THF (1 vol. equiv.). The phases were allowed to separate and the aqueous layer was drained. The reaction mixture was then washed with 10 wt % sodium chloride (51.6 kg, 2 equiv.) and transferred back into the cleaned 200-gallon reactor along with water (128.8 kg, 5 equiv.). To this was added 50 wt % sodium hydroxide solution (18.8 kg, 3.8 equiv.) while maintaining the batch temperature<55° C. The batch was held at 45-55° C. for ~1 h after which time it was sampled and met the specification of ≤2.0% (AUC) of Compound 11 by HPLC, detecting 0.1% (AUC) residual Compound 11.

The reaction was allowed to cool to 25±2° C. and heptane (44.1 kg, 2.5 vol. equiv.) was added. The reaction mixture was stirred for 30 min and settled for 48 min. Three phases were observed: bottom red/brown aqueous layer, middle viscous black layer, and top clear red organic layer. The top organic layer was removed and the middle and bottom product containing layers were combined and washed with another 44.1 kg (2.5 vol. equiv.) of heptane. Once again, three phases were observed and the top organic layer was removed.

While maintaining the temperature≤30° C. the pH of the combined middle and bottom layers was adjusted to pH<1.5 using 37 wt % hydrochloric acid (24.38 kg). MTBE (66.8 kg, 3.5 vol. equiv.) was added, and the mixture was stirred for 30 min before allowing to settle for 20 min. Upon trying to drain the lower aqueous phase, it was observed that the phases had not fully separated. Through experimentation with a small aliquot of the reaction mixture (taken earlier for pH testing), more MTBE (66.7 kg, 3.5 vol. equiv.) was added to the reactor. After stirring for 30 min and allowing the reaction mixture to settle for an additional 2 h, the lower aqueous phase was drained, producing a clean phase separation. The reaction mixture was washed with water (51.5 kg, 2 equiv.) and held overnight for 15 h 10 min before draining the lower aqueous layer. The reaction mixture was filtered through a pad of Celite, and the cake was washed with MTBE (9.53 kg, 0.5 vol. equiv.). The batch was transferred into the 250-liter reactor and 160 L (~6.2 vol. equiv) of solvent was removed by distillation. [Note: The distillation volume was adjusted to account for the extra MTBE added.] Acetonitrile (30.4 kg, 1.5 vol. equiv.) was added and 38-42 L (~1.5 vol. equiv.) of solvent was removed. This was repeated three times. The batch was cooled to 0-5° C. at ~10° C./h, held at temperature for 2 h, and filtered. The cake was then washed with 30.4 kg of pre-chilled acetonitrile (1.5 vol. equiv). After the cake was deliquored and dried at 122° F. (50±5° C.), the product was offloaded to yield crude Ajulemic Acid (5.29 kg actual weight, 21.1% yield, purity: 99.0% (AUC) by HPLC using Method A: see Table 1) as an off-white solid.

TABLE 1

ASSAY AND RELATED SUBSTANCES CHROMATOGRAPHIC CONDITIONS
The HPLC system is operated in the gradient mode.

| | |
|---|---|
| Column | Agilent Zorbax SB-CN, 5 µm, 4.6 × 250 mm, P/N: 880975-905 |
| Flow | 1.5 mL/min |
| Injection Volume | 10 µL |
| Autosampler Temperature | Ambient |
| Column Temperature | Ambient |
| Detection Wavelength | 220 nm |
| Run Time | 37 min |
| Pump A | Water, HPLC grade |
| Pump B | 0.1% Phosphoric Acid in Acetonitrile:Methanol (90:10) |
| Needle Wash | Methanol |

| Gradient Program | | |
|---|---|---|
| Time (min) | Pump A (%) | Pump B (%) |
| 0 | 55 | 45 |
| 20 | 45 | 55 |
| 30 | 0 | 100 |
| 30.1 | 55 | 45 |
| 37 | 55 | 45 |

Step 3

To a 40-liter reactor was charged crude Ajulemic Acid (5.28 kg, 1 equiv.) and heptane (21.8 kg, 6 vol. equiv.). To a 250-liter reactor was charged pyridine (2.18 kg, 2.1 equiv.) and heptane (7.2 kg, 2 vol. equiv.). Both reactors were then heated to 50-60° C. After the contents of the 40-L reactor had dissolved the solution was transferred to the 250-L reactor and additional heptane (7.2 kg, 2 vol. equiv.) was used to rinse the 40-L reactor with this being transferred to the 250-L reactor. While maintaining the batch temperature at 50-60° C., acetic anhydride (2.50 kg, 1.8 equiv.) was added and the reaction mixture was stirred for 2 h. The reaction mixture was sampled and showed 0.8% (AUC) crude Ajulemic Acid, which did not meet the specification of ≤0.5% (AUC). A second sample was obtained after 3 h which passed the specification with 0.2% (AUC) crude Ajulemic Acid detected.

To the reactor was then slowly charged deionized (DI) water (7.40 kg, 1.4 equiv.) while maintaining the temperature at 50±5° C. The reaction mixture stirred for 2 h and analyzed by HPLC to meet the specification of ≤0.5% Acetylated Ajulemic Anhydride (AUC) by HPLC with 0.3% (AUC) Acetylated Ajulemic Acid being detected. The lower aqueous layer was drained and the organic phase was washed with 1N HCl (14.80 kg, 2.8 equiv). The pH of the aqueous layer was 3 and met the specification of pH≤5. The organic layer was washed once more with water (7.40 kg, 1.4 equiv.) to obtain pH 4 which passed the specification of pH≥3. The batch was allowed to cool to 0-5° C. at ~10° C./h overnight, followed by holding for 3 h at 0-5° C. The batch was filtered, washed with pre-cooled heptane (11.2 kg, 3 equiv.), and dried under vacuum at 122° F. (50±5° C.). The product was offloaded and gave Acetylated Ajulemic Acid (5.03 kg actual weight, 86.1% yield) as a white solid with a purity of 99.2% (AUC) by HPLC (Method A).

Step 4

To a 40-liter reactor was charged Acetylated Ajulemic acid (5.02 kg, 1 equiv.), MTBE (15.37 kg, 4.13 vol. equiv.), and 2N NaOH (14.54 kg, 2.400 equiv.) while maintaining the batch temperature≤50° C. The batch was maintained at 45-55° C. for 4 h 2 min after which time the batch had no unreacted Acetylated Ajulemic Acid and met the specification of ≤0.5% (AUC) Acetylated Ajulemic Acid by HPLC. The reaction mixture was allowed to cool to 25° C. While maintaining the batch temperature 25±5° C., the batch was acidified with 37 wt % HCl (3.62 kg, 0.60 vol. equiv.). After stirring for 30 min the lower aqueous layer was separated and the organic layer was washed with water (5.53 kg, 1.1 equiv.). The pH was 2. Two additional water washes were performed and the reaction mixture reached pH 3. Although this did not meet the specification of pH>3, the reaction was continued.

The organic layer was filtered through Celite, a 10-micron filter, and a 2.4 micron filter into a 250-liter reactor. The 40-liter reactor was then washed with MTBE (1.86 kg, 0.5 vol. equiv.) and the batch along with the wash was transferred back into the cleaned 40-liter reactor through a 10-micron and a 2.4 micron filter. MTBE (10 L, 2 vol. equiv.) was distilled off and acetonitrile (17.4 kg, 4.4 vol. equiv.) was added. Then, 22.25 L (~4.4 vol. equiv.) of solvent was distilled off, and the distillate was analyzed by NMR to reveal 46% MTBE. Finally, additional acetonitrile (17.4 kg, 4.4 vol. equiv.) was added and 14.6 L (2.9 vol. equiv.) solvent was distilled off. The distillate was analyzed by NMR to reveal 0.6% MTBE. The temperature was adjusted to 20-30° C. over 9 h 25 min. Crystals were present and reaction mixture was cooled to 0-5° C. over 2 h. It was held for 3 h before the contents were filtered. The mother liquor was recirculated through the reactor several times to facilitate slurry transfer. The crystals were washed with 9.8 kg (2.5 vol. equiv.) of pre-chilled acetonitrile. The product dried in the vacuum oven at 122-130° F. with a slight nitrogen bleed. After 258 hr, the product was assayed by GC and met the specification of ≤200 ppm. The product was offloaded and gave Ajulemic Acid (4.12 kg actual weight, 90.7% yield) with a purity of 99.8% (AUC) by HPLC (Method A).

Receptor Binding

Affinity, or binding affinity, is a measure of the strength of the binding interaction between two or more distinct molecular entities (e.g. between a compound and a receptor) that can be defined by equilibrium binding constants or kinetic binding rate parameters. Examples of suitable constants or parameters and their measurement units are well known in the art and include, but are not limited to, association constant ($K_A$); dissociation constant ($K_D$) or inhibition constant ($K_i$); association rate constant ($K_{on}$) and dissociation rate constant ($K_{off}$). In one embodiment, $K_i$ equals [receptor]·[inhibitor]/[receptor bound by inhibitor], so $K_i$ is an equilibrium constant for the inhibitor binding to the receptor. In the case of $K_A$, higher values mean stronger or greater binding affinity. In the case of $K_i$ (or $K_D$), lower values mean a stronger or greater binding affinity.

The present compounds (e.g., the ultrapure AJA) have a greater affinity for the CB2 receptor than for the CB1 receptor. This means that the present compounds (e.g., the ultrapure AJA) bind more tightly to CB2 than CB1, i.e., with a smaller $K_i(CB2)$ (i.e., $K_i$ for the CB2 receptor) than its $K_i(CB1)$ (i.e., $K_i$ for the CB1 receptor). Likewise, the present compounds (e.g., the ultrapure AJA) have a lesser affinity for the CB1 receptor than for the CB2 receptor. In other words, the present compounds (e.g., the ultrapure AJA) bind less strongly to CB1 than CB2, i.e., with a larger $K_i(CB1)$ than its $K_i(CB2)$.

The affinity of the purified form of ajulemic acid for the CB2 receptor can range from about 5 to about 10-fold greater than the affinity for the CB1 receptor. Ranges from about, 5x-about 50x, about 7x-about 10x, about 8x-about 15x, about 10x-about 20x, about 15x-about 30x, about 25x-about 50x, about 40-about 75x, about 50x-about 100x, about 2x-about 1000x, about 2x-about 800x, about 5x-about 600x, about 10x-about 500x, about 15x-about 300x, about 5x-about 200x, about 10x-about 100x, about 20x-about 80x, or about 10x-about 50x are also encompassed by the invention (ranges represent ratios of affinity of ajulemic acid for CB2 receptor vs. affinity for CB1 receptor, e.g., $K_i(CB1)/K_i(CB2)$.

In some embodiments, the $K_i(CB1)$ (i.e., $K_i$ for the CB1 receptor) of the present compounds (e.g., the ultrapure AJA) may be at least about 2-fold, at least about 3-fold, at least about 4-fold, at least about 5-fold, at least about 8-fold, at least about 10-fold, at least about 50-fold, at least about 100-fold, at least about 200-fold, at least about 400-fold, at least about 500-fold, at least about 1000-fold, at least about 10,000-fold, from about 2-fold to about 10,000-fold, from about 2-fold to about 1,000-fold, from about 5-fold to about 500-fold, from about 5-fold to about 100-fold, from about 7-fold to about 10-fold, from about 8-fold to about 15-fold, from about 10-fold to about 20-fold, from about 15-fold to about 30-fold, from about 25-fold to about 50-fold, from about 40-fold to about 75-fold, or from about 50-fold to about 100-fold, of the $K_i(CB2)$ (i.e., $K_i$ for the CB2 receptor).

The ratio of $K_i(CB1)/K_i(CB2)$ of the present compounds (e.g., the ultrapure AJA) may be at least about 2, at least about 3, at least about 4, at least about 5, at least about 8, at least about 10, at least about 50, at least about 100, at least about 200, at least about 400, at least about 500, at least about 1000, at least about 10,000, from about 2 to about 10,000, from about 2 to about 1,000, from about 5 to about 500, from about 5 to about 100, from about 7 to about 10, from about 8 to about 15, from about 10 to about 20, from about 15 to about 30, from about 25 to about 50, from about 40 to about 75, or from about 50 to about 100.

In certain embodiments, the purified form of AJA has a $K_i$ for the CB2 receptor of about 150 nM or less, about 125 nM or less, about 110 nM or less, about 100 nM or less, about 90 nM or less, about 80 nM or less, about 70 nM or less, about 60 nM or less, about 50 nM or less, about 40 nM or less, or about 30 nM or less.

Any conventional method for measuring receptor binding affinity can be used to assay binding of the ligand to the CB1 or CB2 receptor (see, Pertwee R G. Pharmacological action of cannabinoids. Handbook Exp. Pharmacol 168:1-51 (2005); McPartland et al. Meta-analysis of cannabinoid ligand binding affinity and receptor distribution: interspecies differences. British J. Pharmacology 152:583-593 (2007)).

Binding affinity between two components may be measured directly or indirectly. Indirect measurement of affinity may be performed using surrogate properties that are indicative of, and/or proportional to, affinity. Such surrogate properties include: the quantity or level of binding of a first component to a second component, or a biophysical characteristic of the first component or the second component that is predictive of or correlated to the apparent binding affinity of the first component for the second component. Specific examples include measuring the quantity or level of binding of first component to a second component at a sub-saturating concentration of either the first or the second component. Other biophysical characteristics that can be measured include, but are not limited to, the net molecular charge, rotational activity, diffusion rate, melting temperature, electrostatic steering, or conformation of one or both of the first and second components. Yet other biophysical characteristics that can be measured include determining stability of a binding interaction to the impact of varying temperature, pH, or ionic strength.

Binding affinities can be quantified by measuring the rates of compound/receptor complex formation and dissociation. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ is equal to the dissociation constant $K_D$. (See, generally, Davies et al. (1990) Annual Rev. Biochem. 59:439-473). $K_i$ may be measured by assays such as radioligand binding assays (e.g., procedures as described in Example 4) or similar assays known to those skilled in the art.

The relative affinity for each receptor may be determined by a competition binding assay between labeled compounds and increasing concentrations of unlabeled compounds. The binding affinity can be determined by competition FACS using labeled compound or other competitive binding assays.

The binding affinity of a compound to a receptor can also be determined by surface plasmon resonance (SPR). $K_D$ or $K_i$ may be determined by the BIAcore technology (GE), or the KinExA® (Sapidyne Instruments) affinity analysis.

Conditions to be Treated

The present invention also provides for a method of treating or preventing conditions described herein by administering to a subject the present compound or composition.

Conditions that can be treated or prevented by the present compounds or compositions include, but are not limited to, fibrotic diseases, inflammatory diseases and pain. Fibrotic diseases include, for example, scleroderma, systemic sclerosis, scleroderma-like disorders, sine scleroderma, liver cirrhosis, interstitial pulmonary fibrosis, idiopathic pulmonary fibrosis, Dupuytren's contracture, keloids, cystic fibrosis, chronic kidney disease, chronic graft rejection, fibrosis of organs such as liver, esophagus, heart, lung, intestines, etc., and other scarring/wound healing abnormalities, postoperative adhesions, and reactive fibrosis. Inflammatory diseases include, for example, systemic lupus erythematosus, AIDs, multiple sclerosis, rheumatoid arthritis, psoriasis, Type 1 diabetes, diabetes, cancer, asthma, atopic dermatitis, autoimmune thyroid disorders, ulcerative colitis, Crohn's disease, neurodegenerative diseases such as Alzheimer's disease, Parkinson's disease, stroke and ischemia.

Non-limiting examples of fibrosis include liver fibrosis, lung fibrosis (e.g., silicosis, asbestosis, idiopathic pulmonary fibrosis), oral fibrosis, endomyocardial fibrosis, retroperitoneal fibrosis, deltoid fibrosis, kidney fibrosis (including diabetic nephropathy), cystic fibrosis, and glomerulosclerosis. Liver fibrosis, for example, occurs as a part of the wound-healing response to chronic liver injury. Fibrosis can occur as a complication of haemochromatosis, Wilson's disease, alcoholism, schistosomiasis, viral hepatitis, bile duct obstruction, exposure to toxins, and metabolic disorders. Endomyocardial fibrosis is an idiopathic disorder that is characterized by the development of restrictive cardiomyopathy. In endomyocardial fibrosis, the underlying process produces patchy fibrosis of the endocardial surface of the heart, leading to reduced compliance and, ultimately, restrictive physiology as the endomyocardial surface becomes more generally involved. Oral submucous fibrosis is a chronic, debilitating disease of the oral cavity characterized by inflammation and progressive fibrosis of the submucosal tissues (lamina propria and deeper connective tissues). The buccal mucosa is the most commonly involved site, but any part of the oral cavity can be involved, even the pharynx. Retroperitoneal fibrosis is characterized by the development of extensive fibrosis throughout the retroperitoneum, typically centered over the anterior surface of the fourth and fifth lumbar vertebrae.

Scleroderma is a disease of the connective tissue characterized by fibrosis of the skin and internal organs. Scleroderma has a spectrum of manifestations and a variety of therapeutic implications. It comprises localized scleroderma, systemic sclerosis, scleroderma-like disorders, and sine scleroderma. Systemic sclerosis can be diffuse or limited. Limited systemic sclerosis is also called CREST (calcinosis, Raynaud's esophageal dysfunction, sclerodactyly, telangiectasia). Systemic sclerosis comprises: scleroderma lung disease, scleroderma renal crisis, cardiac manifestations, muscular weakness including fatigue or limited CREST, gastrointestinal dysmotility and spasm, and abnormalities in the central, peripheral and autonomic nervous system.

The major symptoms or manifestations of scleroderma and in particular of systemic sclerosis are inappropriate excessive collagen synthesis and deposition, endothelial dysfunction, vasospasm, collapse and obliteration of vessels by fibrosis.

For example, a compound having the structure as shown in Formula I can be ajulemic acid. In particular, applicants have discovered that administration of ultrapure ajulemic acid is effective in treating tissue fibrosis of the lung and skin, as demonstrated using a well-established animal model of scleroderma without any of the CB1-mediated behavioral side effects.

A therapeutically effective amount of the present compound (e.g., ultrapure ajulemic acid) may lower the level of pain experienced by a subject. In one embodiment, the level of pain experienced by a patient can be assessed by use of a visual analog scale (VAS) or a Likert-type scale. A VAS is a straight line with one end of the line representing no pain and the other end of the line representing the worst imaginable pain. Patients are asked to mark on the line where they considered their pain to be at each time point, and the length from no pain to the mark can be related to the length of the full scale. A Likert-type scale is a rating scale, usually in the range of 1 to 5, based on degrees of agreement or disagreement to statements. A similar type of scale, although based on an 11 point scale (ranging from 0 to 10) can also be used. Such pain scales can be applied to visualize an alteration of the level of pain a patient experiences during treatment, e.g., a reduction of the level of pain a patient or a population of patients experiences before and after initiation of a pain therapy. U.S. Pat. No. 7,413,748. For example, the pain may be reduced by at least about 1 point, at least about 2 points, at least about 3 points, at least about 4 points, at least about 5 points, at least about 6 points, at least about 7 points, or at least about 8 points on an 11-point pain scale. The level of pain may also be assessed by other suitable methods.

A therapeutically effective amount of the present compound (e.g., ultrapure ajulemic acid) may be used to treat or prevent fibrosis. Fibrosis may be assessed using in vitro or in vivo models. In one embodiment, in vitro fibrosis can be assayed by measuring the amount of extracellular matrix protein production in response to TGF-beta, PDGF, CTGF, or other pro-fibrotic factors or through the presence of markers of fibroblast activation. Common endpoints include measurement of collagen, fibronectin, and actin. In another embodiment, in vivo fibrosis is measured by the degree of extracellular matrix production in a particular tissue. In vivo models of fibrosis include chemically induced models in which an external fibrosis mediator such as bleomycin, HOCl, CCl$_4$ or alcohol is used to induce liver, kidney, skin or lung fibrosis. Genetic models of fibrosis are also commonly used including animals which overexpress TGF-beta, PDGF, osteopontin and interleukins, plus the tight skin (tsk) mouse model. Fibrosis may also be assessed by other suitable methods.

A therapeutically effective amount of the present compound (e.g., ultrapure ajulemic acid) may be used to treat or prevent inflammation. Inflammation may be assessed using in vitro or in vivo models. In one embodiment, in vitro inflammation can be assayed by measuring the chemotaxis and activation state of inflammatory cells. In another embodiment, inflammation can be measured by examining the production of specific inflammatory mediators such as interleukins, cytokines and eicosanoids mediators. In yet another embodiment, in vivo inflammation is measured by swelling and edema of a localized tissue or migration of leukocytes. Animal models of inflammation may use a stimulus such as phorbol esters, arachidonic acid, platelet activating factor, zymosan, LPS, thioglycollate or other agents to elicit inflammation in tissues such as ear, paw, skin or peritonium. Inflammation may also be measured by organ function such as in the lung or kidneys and by the production of pro-inflammatory factors. Inflammation may also be assessed by other suitable methods.

Methods of Treatment

The compounds and compositions described herein can be administered to cells in culture, e.g. in vitro or ex vivo, or to a subject, e.g., in vivo, to treat, prevent, and/or diagnose a variety of conditions/diseases as discussed above and further described below.

The term "treat" or "treatment" includes administration of a compound, e.g., by any route, e.g., orally, to a subject. The compound can be administered alone or in combination with, a second compound. Treatments may be sequential, with the present compound being administered before or after the administration of other agents. Alternatively, agents may be administered concurrently. The subject, e.g., a patient, can be one having a disorder (e.g., a disorder as described herein), a symptom of a disorder, or a predisposition toward a disorder. Treatment is not limited to curing or complete healing, but can result in one or more of alleviating, relieving, altering, partially remedying, ameliorating, improving or affecting the disorder, reducing one or more symptoms of the disorder or the predisposition toward the disorder. In an embodiment the treatment (at least partially) alleviates or relieves fibrosis. In one embodiment, the treatment reduces at least one symptom of the disorder or delays onset of at least one symptom of the disorder. The effect is beyond what is seen in the absence of treatment.

The compound effective to treat a disorder refers to an amount of the compound which is effective, upon single or multiple dose administration to a subject, to achieve treatment. The degree of treatment with a therapeutically effective amount encompasses any improvement or cure of a disease as measured by standard clinically relevant criteria.

The amount of a compound effective to prevent a disorder, or "a prophylactically effective amount" of the compound refers to an amount effective, upon single- or multiple-dose administration to the subject, in preventing or delaying the occurrence of the onset or recurrence of a disorder or a symptom of the disorder.

Subjects that can be treated with the compounds and methods of the present invention include both human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc. In an embodiment the animal is other than a rodent, e.g., a rat or mouse, or a non-human primate.

Titration of a Subject

Treatment of subjects can be optimized by titrating the subject, for example, such that treatment can be initiated with sub-optimal or no-effect doses of each compound and increased to determine the optimal dose of ultrapure ajulemic acid for the treatment and/or prevention of fibrotic or inflammatory diseases in the subject.

Treating a subject with ultrapure ajulemic acid can cause side effects such as dizziness, dry mouth, headache, nausea, pallor, somnolence, and vomiting.

The side effects can be modulated to some extent by starting at a low dose and slowly titrating the dose upward, e.g., during the course of treatment, for example over the course of weeks, months or years.

In one embodiment, a subject is titrated to minimize the adverse events and achieve a therapeutic level of the appropriate dosage form of ultrapure ajulemic acid.

Pharmaceutical Compositions

Various dosage forms of the present ultrapure compounds (e.g., ultrapure ajulemic acid) can be used in the methods of the present invention for preventing and/or treating various conditions with a better safety and tolerability profile than the prior ajulemic acid. In certain embodiments, the dosage form is an oral dosage form such as a tablet or capsule or enteric coated tablet or osmotic release capsule or unique combination of excipients. In other embodiments, the dosage form is a liquid, topical patch, gel, ointment, cream, aerosol, or inhaled formulation.

The present compositions may be formulated to deliver over a 24-hour period from about 0.5 mg to about 240 mg, from about 5 mg to about 180 mg, or from about 10 mg to about 120 mg of the present ultrapure compound (e.g., ultrapure ajulemic acid).

In further embodiments, the dosage form includes an additional agent or is provided together with a second dosage form, which includes the additional agent. Exemplary additional agents include an analgesic agent such as an NSAID or opiate, an anti-inflammatory agent or a natural agent such as a triglyceride containing unsaturated fatty acid, or isolated pure fatty acids such as eicosapentaenoic acid (EPA), dihomogamma linolenic acid (DGLA), docosahexaenoic acid (DHA) and others. In additional embodiments, the dosage form comprises a capsule wherein the capsule contains a mixture of materials to provide a desired sustained release formulation.

The dosage forms can include a tablet coated with a semipermeable coating. In certain embodiments, the tablet comprises two layers, a layer containing ultrapure ajulemic acid and a second layer referred to as a "push" layer. The semi-permeable coating is used to allow a fluid (e.g., water) to enter the tablet and erode a layer or layers. In certain embodiments, this sustained release dosage form further comprises a laser hole drilled in the center of the coated tablet. The ajulemic acid or other (3R,4R)-Δ8-tetrahydrocannabinol-11-oic acid containing layer comprises ajulemic acid or another (3R,4R)-Δ8-tetrahydrocannabinol-11-oic acid, a disintegrant, a viscosity enhancing agent, a binding agent and an osmotic agent. The push layer comprises a disintegrant, a binding agent, an osmotic agent and a viscosity enhancing agent.

In another aspect, the invention features a dosage form of ultrapure ajulemic acid that is a controlled release dosage form, which provides controlled release of ultrapure ajulemic acid.

In further embodiments, the dosage form comprises a tablet comprising a biocompatible matrix and ultrapure ajulemic acid. The sustained release dosage form may also comprise a hard-shell capsule containing bio-polymer microspheres that contains the therapeutically active agent. The biocompatible matrix and bio-polymer microspheres each contain pores for drug release and delivery. These pores are formed by mixing the biocompatible matrix of bio-polymer microsphere with a pore forming agent. Each biocompatible matrix or bio-polymer microsphere is made up of a biocompatible polymer or mixture of biocompatible polymers. The matrix and microspheres can be formed by dissolving the biocompatible polymer and active agent (compound described herein) in a solvent and adding a pore-forming agent (e.g., a volatile salt). Evaporation of the solvent and pore forming agent provides a matrix or microsphere containing the active compound. In additional embodiments, the sustained release dosage form comprises a tablet, wherein the tablet contains ultrapure ajulemic acid and one or more polymers and wherein the tablet can be prepared by compressing the ultrapure ajulemic acid and one or more polymers. In some embodiments, the one or more polymers may comprise a hygroscopic polymer formulated with ultrapure ajulemic acid. Upon exposure to moisture, the tablet dissolves and swells. This swelling allows the sustained release dosage form to remain in the upper GI tract. The swelling rate of the polymer mixture can be varied using different grades of polyethylene oxide.

In other embodiments, the sustained release dosage form comprises a capsule further comprising particle cores coated with a suspension of active agent and a binding agent which is subsequently coated with a polymer. The polymer may be a rate-controlling polymer. In general, the delivery rate of the rate-controlling polymer is determined by the rate at which the active agent is dissolved.

Various dosage forms of ultrapure ajulemic acid can be administered to a subject. Exemplary dosage forms include oral dosage forms (e.g., a tablet or capsule), topical dosage forms such as a topical patch, gels, and ointments, ophthalmic dosage forms such as drops or liquid formulations, interstitial dosage forms such as liquid formulations, and inhaled dosage forms such as inhalers, nebulizers, aerosols and sprays.

In certain embodiments, the ultrapure ajulemic acid is formulated into a dosage form wherein a single dosage is from about 0.5 mg to about 120 mg once daily or from about 0.15 mg to about 40 mg up to 3 times daily.

In other embodiments, the ultrapure ajulemic acid is formulated into a dosage form wherein a single dosage is from about 0.01 to about 1.5 mg/kg weight of the subject. In further embodiments, the dosage form is administered up to 3 times daily and from about 0.003 to about 0.5 mg/kg weight of the subject.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition may be administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

In an embodiment, one or more of the therapeutic agents that can be used in the methods of the present invention for preventing and/or treating conditions discussed above are formulated with a pharmaceutically acceptable carrier, vehicle or adjuvant. The term "pharmaceutically acceptable carrier, vehicle or adjuvant" refers to a carrier, vehicle or adjuvant that may be administered to a subject, together with the present compounds, and which does not destroy the pharmacological activity thereof and is nontoxic when administered in doses sufficient to deliver a therapeutic amount of the compound.

The compound may be formulated as a salt such as a pharmaceutically acceptable salt form, which includes, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Pharmaceutically acceptable salts also include base addition salts which may be formed when acidic protons present are capable of reacting with inorganic or organic bases. Suitable pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the invention. *Handbook of Pharmaceutical Salts: Properties, and Use* (P. H. Stahl & C. G. Wermuth eds., Verlag Helvetica Chimica Acta, 2002) [1].

Pharmaceutically acceptable carriers, adjuvants and vehicles that may be used in the dosage forms of this invention include, but are not limited to, ion exchangers, alumina, aluminum stearate, lecithin, self-emulsifying drug delivery systems (SEDDS) such as d-E-tocopherol polyethylene-glycol 1000 succinate; surfactants used in pharmaceutical dosage forms such as Tweens or other similar polymeric delivery matrices; serum proteins such as human serum albumin; buffer substances such as phosphates, glycine, sorbic acid, potassium sorbate, partial glyceride mixtures of saturated vegetable fatty acids, water, salts; or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxmethylcellulose, polyacrylates, waxes, polyethylene-polyoxypropylene-block polymers, polyethylene glycol and wool fat. Cyclodextrins such as alpha, beta and γ-cyclodextrin, or chemically modified derivatives such as hydroxyalkylcyclodextrins, including 2- and 3-hydroxypropyl-beta cyclodextrins, or other solubilized derivatives may also be advantageously used to enhance delivery of compounds of the formulae described herein that can be used in the methods of the present invention for preventing and/or treating fibrotic conditions. Additional suitable excipients may be found in Handbook of Pharmaceutical Excipients, R. C. Rowe, et. al., Pharmaceutical Press, 2009 [9]. In certain embodiments, unit dosage formulations are compounded for immediate release, though unit dosage formulations compounded for delayed or prolonged release of one or both agents are also disclosed.

In one embodiment, the therapeutic agents that can be used in the present methods are formulated in a single unit dose such that the agents are released from the dosage at different times.

In another embodiment, for example, where one or more of the therapeutic agents is administered once or twice per day, the agent is formulated to provide extended release. For example, the agent is formulated with an enteric coating. In an alternative embodiment, the agent is formulated using a biphasic controlled release delivery system, thereby providing prolonged gastric residence. For example, in some embodiments, the delivery system includes (1) an inner solid particulate phase formed of substantially uniform granules containing a pharmaceutical having a high water solubility, and one or more hydrophilic polymers, one or more hydrophobic polymers and/or one or more hydrophobic materials such as one or more waxes, fatty alcohols and/or fatty acid esters, and (2) an outer solid continuous phase in which the above granules of inner solid particulate phase are embedded and dispersed throughout, the outer solid continuous phase including one or more hydrophobic polymers, one or more hydrophobic polymers and/or one or more hydrophobic materials such as one or more waxes, fatty alcohols and/or fatty acid esters, which may be compressed into tablets or filled into capsules. In some embodiments, the agent is incorporated into polymeric matrices comprised of hydrophilic polymers that swell upon imbibition of water to a size that is large enough to promote retention of the dosage form in the stomach during the fed mode.

The ultrapure ajulemic acid in the formulation may be formulated as a combination of fast-acting and controlled release forms. For example, the ultrapure ajulemic acid is formulated with a single release property. For example, it is not present in a modified release form, e.g., a controlled release form.

The present compositions may be taken just prior to or with each of three meals, each of two major meals, or one meal. In other embodiments, a composition disclosed herein can be administered once a day or twice a day and need not be administered just before or with a meal.

The dosage forms of this invention that can be used in the present methods may be administered orally, parentally, by inhalation spray, topically, rectally, interstitially, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The dosage forms that can be used in the present methods may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The present compounds or compositions may be administered orally, for example as a component in a dosage form. The dosage forms may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The dosage forms of this invention may be orally administered in any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The dosage forms of this invention may also be administered in the form of suppositories for rectal administration. These compositions can be prepared by mixing a compound of this invention that can be used in the methods of the present invention for preventing and/or treating fibrotic conditions with a suitable non-irritating excipient which is solid at room temperature but liquid at the rectal temperature and therefore will melt in the rectum to release the active components. Such materials include, but are not limited to, cocoa butter, beeswax and polyethylene glycols.

Ophthalmic administration of the dosage forms of this invention is useful when the desired treatment involves areas or organs readily accessible by ophthalmic application. Ophthalmic administration, the composition could be applied by instillation of a cream, an ointment, or a liquid drop preparation in the conjunctival sac.

Topical administration of the dosage forms of this invention is useful when the desired treatment involves areas or organs readily accessible by topical application. For application topically to the skin, the dosage form should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition that can be used in the methods of the present invention can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The dosage forms of this invention that can be used in the methods of the present invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the dosage forms of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

In certain embodiments, the dosage form that can be used in the methods of the present invention comprises a capsule wherein the capsule comprises a mixture of material to provide the desired sustained release.

In other embodiments, the dosage form that can be used in the methods of the present invention comprises a tablet coated with a semipermeable coating. In certain embodiments, the tablet comprises two layers, a layer containing ultrapure ajulemic acid and a second layer referred to as a "push" layer. The semi-permeable coating is used to allow a fluid (e.g., water) to enter the tablet and erode a layer or layers. In certain embodiments, the sustained release dosage form further comprises a laser hole drilled in the center of the coated tablet. The ultrapure ajulemic acid containing layer comprises ultrapure ajulemic acid, a disintegrant, a viscosity enhancing agent, a binding agent and an osmotic agent. The push layer comprises a disintegrant, a binding agent, an osmotic agent and a viscosity-enhancing agent.

In further embodiments, the dosage form that can be used in the methods of the present invention comprises a tablet comprising a biocompatible matrix and an ultrapure ajulemic acid. The sustained release dosage form may also comprise a hard-shell capsule containing bio-polymer microspheres that contains the therapeutically active agent.

The biocompatible matrix and bio-polymer microspheres each contain pores for drug release and delivery. These pores are formed by mixing the biocompatible matrix or bio-polymer microsphere with a pore forming agent. Each biocompatible matrix of bio-polymer microsphere is made up of a biocompatible polymer or mixture of biocompatible polymers. The matrix and microspheres can be formed by dissolving the biocompatible polymer and active agent (compound described herein) in a solvent and adding a pore forming agent (e.g., a volatile salt). Evaporation of the solvent and pore forming agent provides a matrix or microsphere containing the active compound.

The sustained release dosage form that can be used in the methods of the present invention comprises a tablet, wherein the tablet contains ultrapure ajulemic acid and one or more polymers and wherein the tablet can be prepared by compressing the ultrapure ajulemic acid and one or more polymers. In some embodiments, the one or more polymers may comprise a hygroscopic polymer formulated with the ultrapure ajulemic acid active agent (i.e., a compound described herein). Upon exposure to moisture, the tablet dissolves and swells. This swelling allows the sustained release dosage form to remain in the upper GI tract. The swelling rate of the polymer mixture can be varied using different grades of polyethylene oxide.

In other embodiments, the sustained release dosage form that can be used in the methods of the present invention comprises a capsule further comprising particle cores coated with a suspension of active agent and a binding agent which is subsequently coated with a polymer. The polymer may be a rate-controlling polymer. In general, the delivery rate of the rate-controlling polymer is determined by the rate at which the active agent is dissolved.

Non-limiting examples of capsules include but are not limited to gelatin capsules, HPMC, hard shell, soft shell, or any other suitable capsule for holding a sustained release mixture. The solvents used in the above sustained release dosage forms include, but are not limited to ethyl acetate, triacetin, dimethyl sulfoxide (DIV1S0), propylene carbonate, N-methylpyrrolidone (NMP), ethyl alcohol, benzyl alcohol, glycofurol, alpha-tocopherol, Miglyol 810, isopropyl alcohol, diethyl phthalate, polyethylene glycol 400 (PEG 400), triethyl citrate, and benzyl benzoate.

The viscosity modifiers used in the above sustained release dosage forms include, but are not limited to caprylic/capric triglyceride (Migliol 810), isopropyl myristate (IPM), ethyl oleate, triethyl citrate, dimethyl phthalate, benzyl benzoate and various grades of polyethylene oxide. The high viscosity liquid carrier used in the above sustained release dosage forms include, but are not limited to sucrose acetate isobutyrate (SAIB) and cellulose acetate butyrate (CAB) 381-20.

Non-limiting examples of materials that make up preferred semi-permeable layers include, but are not limited to cellulosic polymers such as cellulose acetate, cellulose acylate, cellulose diacylate, cellulose triacylate, cellulose diacetate, cellulose triacetate or any mixtures thereof; ethylene vinyl acetate copolymers, polyethylene, copolymers of ethylene, polyolefins including ethylene oxide copolymers (e.g., Engage®—Dupont Dow Elastomers), polyamides, cellulosic materials, polyurethanes, polyether blocked amides, and copolymers (e.g., PEBAX®, cellulosic acetate butyrate and polyvinyl acetate). Non-limiting examples of disintegrants that may be employed in the above sustained release dosage forms include but are not limited to croscarmellose sodium, crospovidone, sodium alginate or similar excipients.

Non-limiting examples of binding agents that may be employed in the above sustained release dosage forms include but are not limited to hydroxyalkylcellulose, a hydroxyalkylalkylcellulose, or a polyvinylpyrrolidone.

Non-limiting examples of osmotic agents that may be employed in the above sustained release dosage forms include but are not limited to, sorbitol, mannitol, sodium chloride, or other salts. Non-limiting examples of biocompatible polymers employed in the above sustained release dosage forms include but are not limited to poly(hydroxyl acids), polyanhydrides, polyorthoesters, polyamides, polycarbonates, polyelkylenes, polyelkylene glycols, polyalkylene oxides, polyalkylene terepthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly(valeric acid), and poly(lactide-co-caprolactone), ethylene vinyl acetate, copolymers and blends thereof.

Non-limiting examples of hygroscopic polymers that may be employed in the above sustained release dosage forms include but are not limited to polyethylene oxide (e.g., Polyox® with MWs from 4,000,000 to 10,000,000), cellulose hydroxymethyl cellulose, hydroxyethyl-cellulose, crosslinked polyacrylic acids and xanthum gum.

Non-limiting examples of rate-controlling polymers the may be employed in the above sustained release dosage forms includes but is not limited to polymeric acrylate, methacrylatelacquer or mixtures thereof, polymeric acrylate lacquer, methacrylate lacquer, an acrylic resin comprising a copolymer of acrylic and methacrylic acid esters or an ammonium methacrylate lacquer with a plasticizer.

Kits

A dosage form described herein may be provided in a kit. The kit includes (a) a compound used in a method described herein, and, optionally (b) informational material. The informational material can be descriptive, instructional, marketing or other material that relates to the methods described herein and/or the use of the dosage form for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to use a compound described herein in a suitable manner to perform the methods described herein, e.g., carry out a reaction to produce a compound described herein.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a dosage form described herein, the composition of the kit can include other ingredients, such as a solvent or buffer, a stabilizer, a preservative, a flavoring agent (e.g., a bitter antagonist or a sweetener), a fragrance, a dye or coloring agent, for example, to tint or color one or more components in the kit, or other cosmetic ingredient, and/or a second agent for treating a condition or disorder described herein. Alternatively, the other ingredients can be included in the kit, but in different compositions or containers than a compound described herein. In such embodiments, the kit can include instructions for admixing a compound described herein and the other ingredients, or for using a compound described herein together with the other ingredients.

In some embodiments, the components of the kit are stored under inert conditions (e.g., under Nitrogen or another inert gas such as Argon). In some embodiments, the components of the kit are stored under anhydrous conditions (e.g., with a desiccant). In some embodiments, the components are stored in a light blocking container such as an amber vial.

A dosage form described herein can be provided in any form, e.g., liquid, dried or lyophilized form. It is preferred that a compound described herein be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a dosage form described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the dosage form is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a dosage form described herein.

The containers of the kits can be air tight, waterproof (e.g., impermeable to changes in moisture or evaporation), and/or light-tight.

The kit optionally includes a device suitable for use of the dosage form, e.g., a syringe, pipette, forceps, measured spoon, swab (e.g., a cotton swab or wooden swab), or any such device.

Thus, specific compositions and ultrapure tetrahydrocannabinol-11-oic acids have been disclosed. A number of embodiments of the invention have been described. Nevertheless, it will be understood that various modifications may be made without departing from the spirit and scope of the invention. Accordingly, other embodiments are within the scope of the following claim. It should be apparent, however, to those skilled in the art that many more modifications besides those already described are possible without departing from the inventive concepts herein. The inventive subject matter, therefore, is not to be restricted except in the spirit of the disclosure. All patents, patent publications and publications mentioned herein are incorporated herein by reference in their entirety to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

EXAMPLES

The following examples are provided in order to demonstrate and further illustrate certain preferred embodiments and aspects of the present invention and are not to be construed as limiting the scope thereof.

Example 1

Evaluation of Ultrapure AJA in Regards to CB1 and CB2

Ultrapure ajulemic acid (JBT-101) was synthesized and its binding to CB1 and CB2 receptors was compared to that of previous preparations.

With respect to ultrapure AJA, there is a significant difference in its $K_i$ in regards to CB1 and CB2. In one particular embodiment, as shown in FIG. 9, the binding affinity of ultrapure AJA for CB2 is about 10× to 20× greater than the binding affinity for CB1. For comparison, FIG. 9 shows various other Ki and Ki(CB1)/Ki(CB2) ratios for various other cannabinoids and other previous synthetically produced AJA [10, 11].

Example 2

Direct Comparisons of AJA vs. THC in the Same Studies
1. Binding-CB1/CB2* CB2 binding is a highly desirable property since it appears to mediate anti-inflammatory and anti-fibrotic effects without psychotropic action.
2. Ring test-Cataleptic response generally accepted as a psychotropic effect mediated by CB1 agonist activity at the level of the brain. Each compound was tested at various therapeutic doses. [11]
3. In vivo Cancer. AJA shows a small but significant inhibition of tumor growth greater than that produced by THC. The doses chosen were in the anti-inflammatory range [12].
4. PK Data. While it shows some cannabinoid-like CNS activity at higher doses, it exhibits a superior therapeutic index compared to other cannabinoid compounds, which may reflect a relatively reduced CNS penetration [3]. Moreover, the pharmacokinetic analysis indicates that although there is some brain penetration in the rat, it is restricted to a degree, with peak levels in the brain, measured at the peak pharmacodynamic time points, reaching only 25-30% of those seen in the plasma. This contrasts with the profile observed with WIN55,212-2 and THC which show a significantly higher relative brain penetration, with brain levels reaching 100-190% of those seen in the plasma. These data complement the recent findings in man in which AJA was found to reduce pain scores in neuropathic pain patients in the absence of *cannabis*-like psychotropic adverse events [13].

Example 3

Study of Ultrapure AJA's Activity on CB1 and CB2 Receptors

Ultrapure ajulemic acid (JBT-101) was evaluated for its pharmacological effects in mice, as well as for functional in vitro activation of CB1 and CB2 cannabinoid receptors.

Specifically, JBT-101 was assessed for its ability to stimulate [35S]GTPγS turnover in CB1 and CB2 receptors in vitro. The compound was also assessed for its antinociceptive effects in a hot plate assay and for cataleptic effects in a ring immobility test, both in female CD-1 mice. Rectal temperature was also measured in these mice.

Introduction of Methods Used

Hot Plate Test for Antinociception

The hot-plate test was used to measure the analgesic activity of ultrapure AJA and other pharmacologic agents based on the reaction time of mice to lick their forepaws and/or jump after being placed on an aluminum hot plate heated to, and maintained at, 54° C.-56° C. Kitchen I and Green P G, Differential Effects of DFP Poisoning and Its Treatment on Opioid Antinociception in the Mouse, Life Sci. 33:669-672 (1983). This test has been shown to measure CB1 agonist activity.

An aluminum surface was maintained at 55° C.±1° C. by circulating water through the passages in the metal. A clear plastic cylinder, 18 cm in diameter and 26 cm high, was placed on the surface to prevent escape. The end point was taken as the time when the mouse either performed a hind paw lick or jumped off the surface; in no case were the animals kept more than 30 seconds on the plate. Mice were never used more than one time; control values and test values were measured, e.g., 3 hours apart. Ultrapure AJA and other test compounds were administered orally about ninety (90) minutes before the hot plate test. The percent change in response time (latency) was calculated by comparing the mean of the control values with the mean of the test values and statistical significance determined by a paired t test.

A dose response was conducted for ultrapure AJA at doses from 0.05 to 56 mg/kg. The ultrapure AJA required much higher doses than the AJA from U.S. Pat. No. 5,338,753 to see analgesia.

Measurement of Cataleptic Effects

The cataleptic response was measured using the ring test described by Pertwee (Pertwee R G, The Ring Test. A Quantitative Method of Assessing the Cataleptic Effect of *Cannabis* in Mice, Br. J. Pharmacol. 46:753-763 (1972)). Mice were placed on a horizontal wire ring 5.5 cm in diameter attached to a 16 cm vertical rod. The hind paws and fore paws were placed at opposite sides of the ring. The ambient temperature was maintained at 30° C. and the environment was free of auditory stimuli and bright lights. The response was calculated as the fraction of time the mouse was immobile over a five (5) minute test period.

A dose response was conducted for ultrapure AJA to oral doses of 0.05 to 56 mg/kg. The ultrapure AJA required much higher doses then the AJA (3a) from the U.S. Pat. No. 5,338,753 to see catalepsy.

GTP-gamma-S Assay

When the CB1 or CB2 receptor is activated by an agonist, the affinity of the G protein alpha subunit increases with respect to GTP vs. GDP. As a consequence, GDP is displaced from the G protein and GTP or GTPγS binds. If a radioactive label, such as [$^{35}$S], is attached to the GTPγS molecule, then the formation of the G protein/[$^{35}$S]GTPγS complex can be directly measured using liquid scintillation spectrophotometry. Weiland et al., (1994) Methods Enzymol 237:3-13. Griffin et al., PET 285:553-560, 1998.

Figure 13:
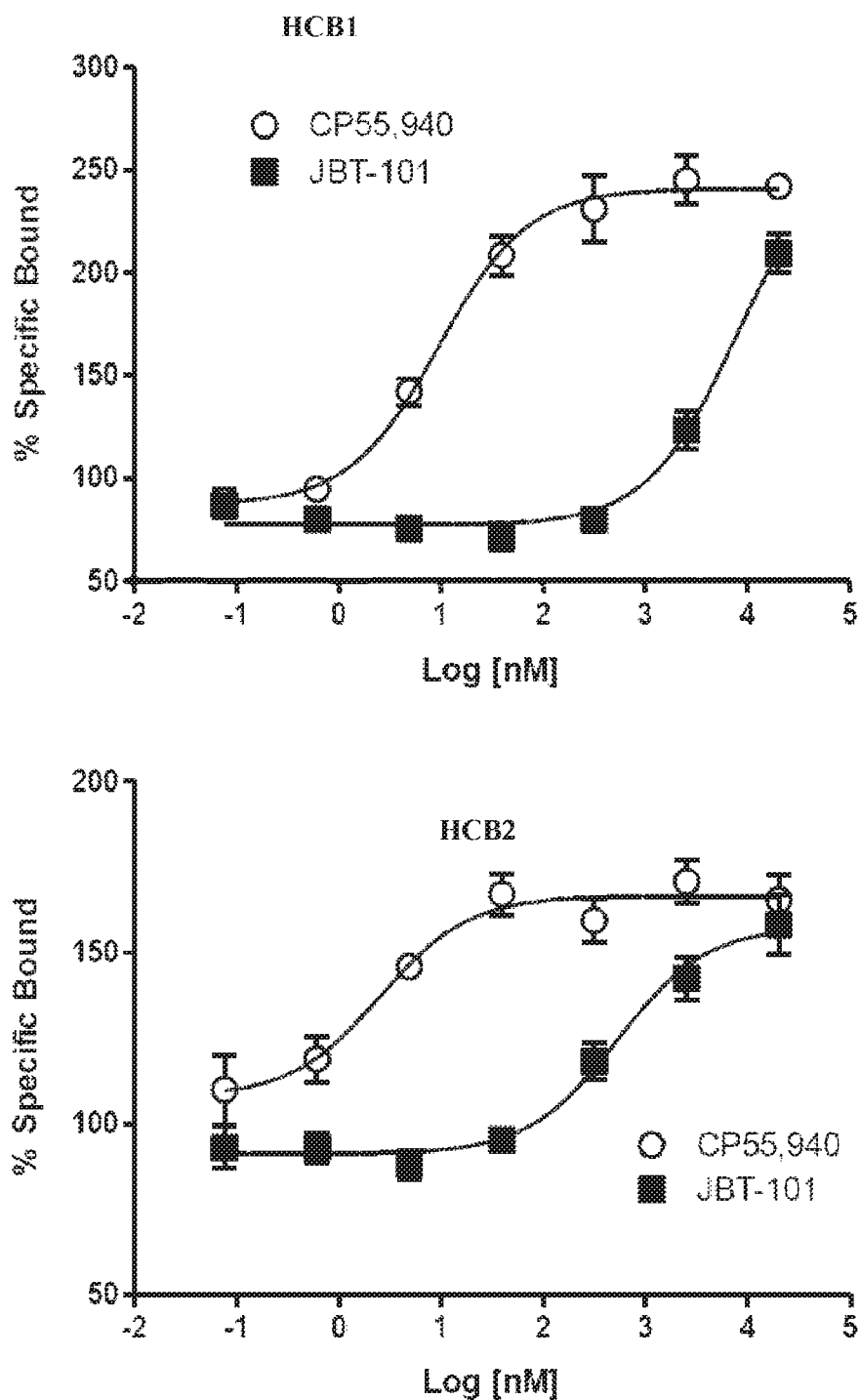
FIG. 13 demonstrates effects of CP55940 (circles) and JBT-101 (ultrapure AJA; squares) on [$_{35}$S]GTPγS turnover in $hCB_1$ and $hCB_2$ receptors (upper and lower panels, respectively) expressed in HEK-293 cells. Each concentration-effect curve represents the mean (±SEM) of 4 repetitions. Conditions used were adapted from Wiley et al. (20).

A GTP-gamma-S assay was used to study the functional activity of AJA on human CB1 and CB2 receptors to further determine the selectivity of ultrapure AJA for the CB2 receptor. As shown in FIG. 13, the potency of ultrapure AJA in the GTP-gamma-S assay was ~10× better in the CB2 assay than in the CB1 assay which further supporting the improved selectivity of ultrapure AJA for CB2 vs CB1.

Experimental Details
Preparation of Stock Solutions for In Vitro Functional Assay For in vitro functional assays, the JBT-101 stock solution was prepared in ethanol or DMSO.

Preparation of Solutions for In Vivo Testing $\Delta^9$-THC [National Institute on Drug Abuse (NIDA), Rockville, Md.], indomethacin (Sigma-Aldrich, St. Louis, Mo.), and JBT-101 were dissolved in a vehicle of peanut or safflower oil (food grade). Compounds were administered at a volume of 20 μl/kg via oral gavage.

In Vitro Functional Assay at Cannabinoid Receptors
Materials and Methods

The CB1 and CB2 receptor assays involve membrane preparations purchased from Perkin Elmer (Waltham, Mass.) isolated from a HEK-293 expression system. G-protein coupled signal transduction (GTP-γ-[35S]) assays of test compounds were conducted in an incubation mixture consisting of a test compound (250 nM-1 mM), GDP (20 μM), GTP-γ-[35S] (100 pM), and the hCB1 and hCB2 membrane preparations (0.4 pM) in a total volume of 0.4 mL of assay buffer (50 mM TRIS-HCl, pH 7.4, 1 mM EDTA, 100 mM NaCl, 5 mM MgCl2, 0.5% (w/v) BSA). Nonspecific binding was determined in the presence of 100 μM unlabeled GTP-γ-S, and basal binding was determined in the absence of drug. Duplicate samples were incubated for 1 h at 30° C., and the bound complex was filtered from the reaction mixture as described previously and counted in a liquid scintillation counter. Specific binding was calculated by subtracting nonspecific binding from total binding and dividing by the total basal binding minus nonspecific binding. Data were plotted and analyzed with GraphPad Prism (GraphPad Software, Inc., San Diego, Calif.).

In Vitro Assays: Results and Discussion

CP55940 (positive control) stimulated GTP-γ-35S turnover through both the hCB1 receptor and the hCB2 receptor at nM concentrations (Table 2; EC50=9.99±2.5 nM for CB1 and EC50=3.96±1.3 nM for CB2). These results indicate that CP55,940 acts as agonists at these G-protein coupled receptor sites (FIG. 13, upper panel). JBT-101 also stimulated GTP-γ-35S turnover through both cannabinoid receptors, but did so with much less potency (FIG. 13, lower panel). The EC50 for JBT-101 at the CB1 receptor was 9209±2042 nM whereas the EC50 at the CB2 receptor was 1020±92 nM (Table 2). The 9-fold difference in potency for activation of CB2 versus CB1 receptors is consistent with the 12-fold selectivity of this compound for binding CB2 receptors, suggesting that JBT-101 would activate CB2 receptors at doses that are not active at CB1 receptors.

TABLE 2

GTP-γ-35S turnover in hCB1 and hCB2 receptors.

| | hCB$_1$ EC$_{50}$ (nM) | | | | |
|---|---|---|---|---|---|
| Compound | Rep 1 | Rep 2 | Rep 3 | Rep 4 | Mean (±SEM) |
| CP55, 940 | 6.989 | 6.294 | 9.529 | 17.14 | 9.99 (2.5) |
| JBT-101 | 13694 | 5830 | 11647 | 5664 | 9209 (2042) |

| | hCB$_2$ EC$_{50}$ (nM) | | | | |
|---|---|---|---|---|---|
| Compound | Rep 1 | Rep 2 | Rep 3 | Rep 4 | Mean (±SEM) |
| CP55, 940 | 2.81 | 0.69 | 5.91 | 6.41 | 3.96 (1.3) |
| JBT-101 | 930 | 815 | 1232 | 1101 | 1020 (92) |

Mouse In Vivo Tests
Subjects

Female CD-1 mice (20-25 g), obtained from Charles River (Raleigh, N.C.), were used for assessment in hot plate nociception, rectal temperature, and ring immobility assays. Separate mice were used for testing each dose of each compound in this battery of procedures. The mice had free access to food and water when in their home cages. All animals were kept in a temperature-controlled (20-22° C.) environment with a 12-hour light-dark cycle (lights on at 7 a.m.).

In Vivo Methods

Each mouse was tested in a battery of three tests, in which cannabinoid CB1 agonists produce in vivo effects in mice (Martin et al., 1991): antinociception (hot plate assay), decreased rectal temperature and ring immobility. Prior to administration of the test compound, rectal temperature and baseline latency in the hot plate test were measured in the mice. The latter procedure involved placing the mouse on a heated surface (mouse cold/hot plate analgesia apparatus; Stoelting, Wood Dale, Ill.) at a setting of 55° C. Time until the mouse lifts or licks a paw was measured, whereupon the mouse was removed from the apparatus. If the mouse did not lift or lick a paw within 30 sec, it was removed from the apparatus and a latency of 30 sec was recorded. After measurement of baseline temperature and hot plate latency, mice were administered vehicle or drug via oral gavage. Hot plate latency and temperature were measured again at 90 minutes after administration (via oral gavage) of peanut oil vehicle or JBT-101 or at 60 minutes after administration (via oral gavage) of Δ9-THC or indomethacin. Subsequently, the mice were placed on a 5.5 cm ring attached at a height of 16 cm to a ring stand, and the amount of time the animals remained motionless during a 5 min period was recorded. In addition, the number of times the mouse fell or jumped off the ring was recorded. If the mouse fell off the ring more than 5 times, the test was terminated.

Data Analysis.

Rectal temperature values were expressed as the difference between control temperature (before injection) and temperature following drug administration (Δ° C.). Antinociception was expressed as the percent maximum possible effect (MPE) using a 30-s maximum test latency as follows: [(test−control)/(30−control)]×100. During assessment for catalepsy, the total amount of time (in seconds) that the mouse remained motionless on the ring apparatus (except for breathing and whisker movement) was measured and was used as an indication of catalepsy-like behavior. This value was divided by 300 s and multiplied by 100 to obtain a percent immobility. If the mouse fell off the ring more than 5 times, the test was terminated and ring immobility data for the mouse were not included in analysis. Separate between-subjects ANOVAs were used to analyze each measure. Significant differences from control (vehicle) were further analyzed with Tukey post hoc tests (α=0.05) as necessary.

In Vivo Tests: Results and Discussion

Figure 14:
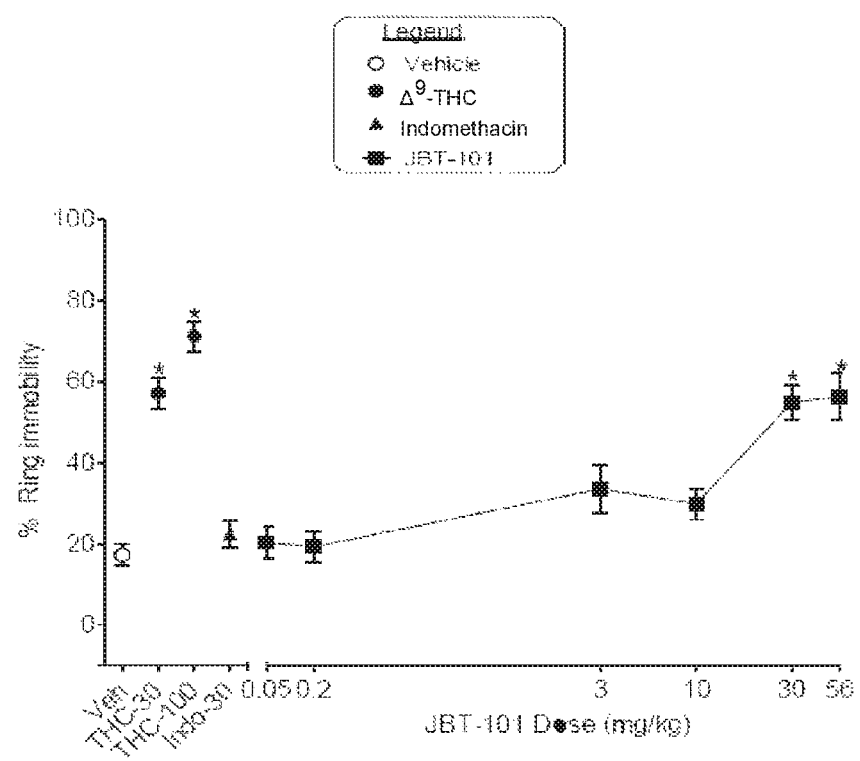
FIG. 14 shows that JBT-101 is active in the ring test only at high doses of 30 mg/kg and above. All drugs were given orally in oil. Conditions as reported by Wiley JL and Martin B R (21). This effect is considered to be CB1 mediated.
Figure 15:
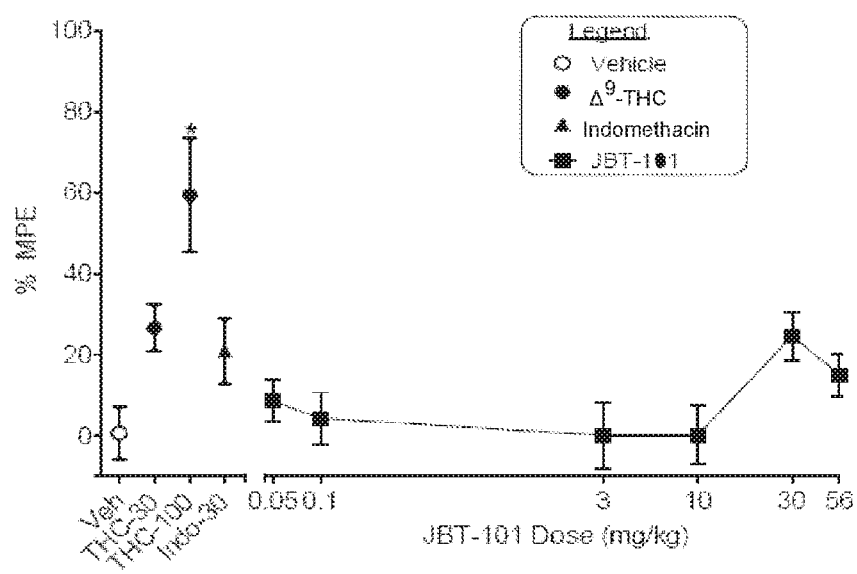
FIG. 15 shows that JBT-101 is active in the mouse hot plate assay only at high doses of 30 mg/kg and above. By comparison, HU-239 (i.e., AJA reported in U.S. Pat. No. 5,338,753) was active at low doses given orally (<0.5 mg/kg). MPE: maximum possible effect. Experimental conditions as reported in Burstein, et al. (22).
Figure 16:
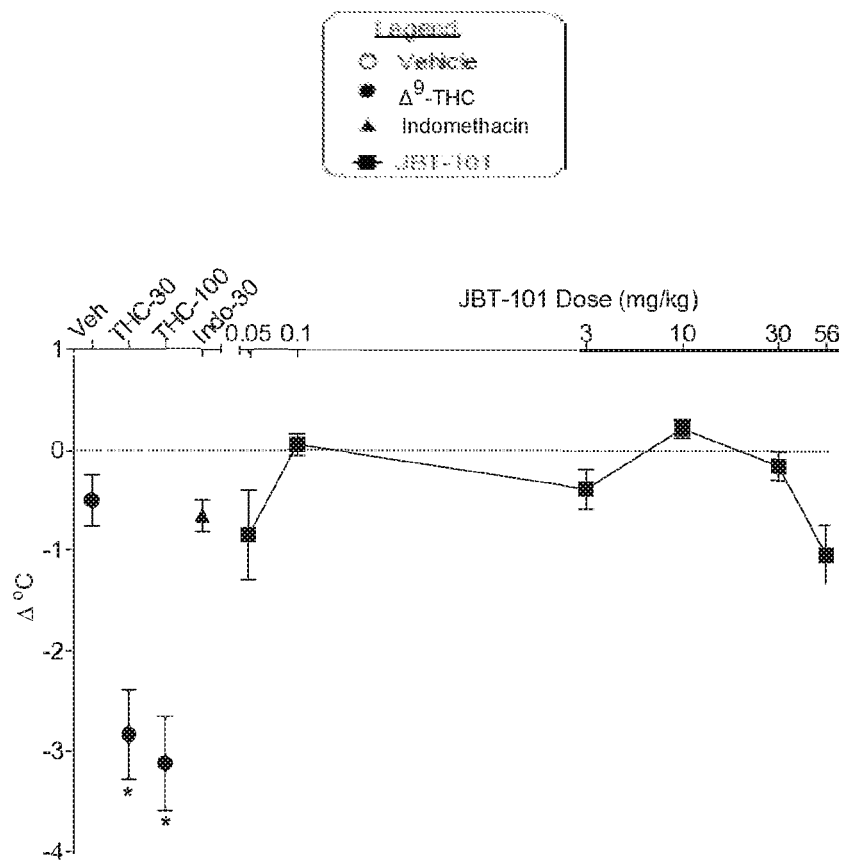
FIG. 16 shows that JBT-101 is inactive in the mouse hypothermia assay. All drugs were given orally in oil. Experimental conditions as reported by Wiley JL and Martin B R (21). This effect is considered to be CB1-mediated.
Figure 17:
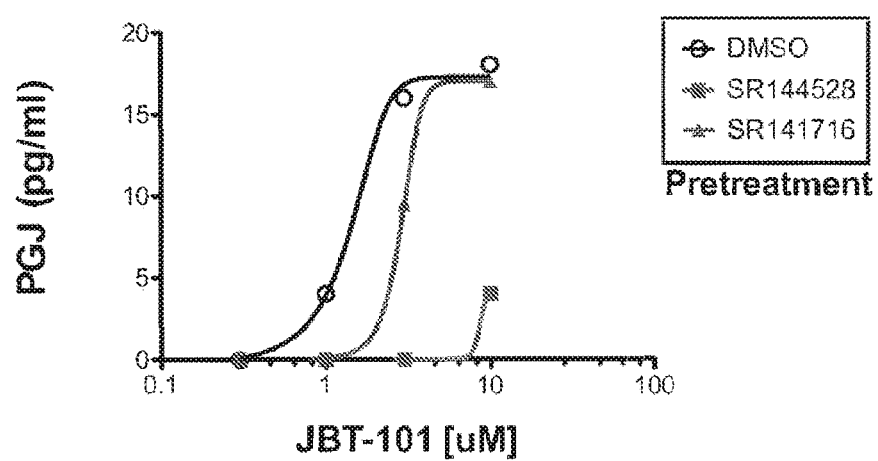
FIG. 17 shows the CB2 specificity of ultrapure JBT-101 in stimulation of PGJ in HL-60 cells. The CB2 antagonist SR144528 reduced ultrapure AJA-induced PGJ synthesis in HL60 immune system cells at low concentrations (squares). The CB1 antagonist SR141716 has a much smaller effect (triangles). DMSO control (open circles). Treatments of cells was carried out in 48 well plates with 20,000 cells/500 μl RPMI/FCS media/well. Cells were incubated for 20 hrs at 37° C. and 5% $CO_2$. Media was changed to 500 μl of serum free RPMI and TNFα (10 nM) added. Treated for 2 hrs with SR144528 [1 μM] or SR141716 [10 μM] and 100 μl removed for ELISA assays. N=4.

Control tests revealed that peanut oil vehicle (negative control) was not active in any of the three tests (hot plate, rectal temperature and catalepsy) [FIGS. 14, 15 and 16, left side of each panel]. A 30 mg/kg dose of indomethacin also did not significantly affect any of the three measures. In contrast, at oral doses of 30 and/or 100 mg/kg, Δ9-THC (positive control) produced significant antinociception [100 mg/kg only; F(9,50)=5.71, p<0.05. FIG. 15], ring immobility [both doses; F(9,48)=21.18, p<0.05. FIG. 14], and hypothermia [both doses; F(9,50)=15.08, p<0.05. FIG. 16], with each measure compared to vehicle condition. JBT-101 was assessed in the three in vivo tests at oral doses ranging from 0.05-56 mg/kg. None of the doses tested produced significant antinociception in the hot plate test (FIG. 15, right side)

or change in rectal temperature (FIG. 16, right side). At oral doses of 30 and 56 mg/kg, JBT-101 significantly increased percent ring immobility in the catalepsy test, as compared to vehicle condition (FIG. 14, right side. $F(9,48)=21.18$, $p<0.05$]. The magnitude of increase was similar at 30 and 56 mg/kg doses and approximated the increase observed at the 30 mg/kg dose of Δ9-THC. Lower doses of JBT-101 (up to 10 mg/kg) did not affect this measure.

In summary, the pattern of effects produced by JBT-101 (0.05-56 mg/kg) in the hot plate and rectal temperature tests in mice did not resemble those exhibited by Δ9-THC (present study; Martin et al., 1991) and other psychoactive cannabinoids, including aminoalkylindoles (Compton et al., 1992a), bicyclic cannabinoids (Compton et al., 1992b), and indole- and pyrrole-derived cannabinoids (Wiley et al., 1998; Wiley et al., 2012). Although JBT-101 increased ring immobility at higher doses (30 and 56 mg/kg), with a magnitude similar to that produced by 30 mg/kg Δ9-THC, its overall pattern of pharmacological effects did not suggest Δ9-THC-like psychoactivity.

SUMMARY

The profile of pharmacological effects produced by JBT-101 (ultrapure ajulemic acid) differs significantly from previously reported effects of ajulemic acid. Previously synthesized (non-purified) ajulemic acid has shown efficacy in several preclinical models of pain and inflammation (reviewed in Wiley, 2005); however, it also produced a profile of pharmacological effects in vivo that is characteristic of Δ9-THC and other psychoactive CB1 receptor agonists. These effects included suppression of spontaneous activity, antinociception, hypothermia, and catalepsy in mice and Δ9-THC-like discriminative stimulus effects in rats (Vann et al., 2007). These effects are consistent with the good CB1 receptor binding affinities exhibited by these earlier ajulemic acid synthesis products: Ki=5.7 nM for Novartis compound (Dyson et al., 2005) and Ki=32.3 nM for HU-239 (Pertwee et al., 2010). Further, the ratio of CB1/CB2 binding for these compounds was low (0.10 and 0.19, respectively). In contrast, JBT-101 showed more than 12-fold selective binding affinity at the CB2 receptor (Ki=51±11 nM) as compared to the CB1 receptor (Ki=628±6 nM). As shown herein, JBT-101 also exhibited similar selectivity for activation of CB2 receptors as compared to CB1 receptors. Furthermore, at doses up to 56 mg/kg (p.o.), behavior effects that are characteristically observed following administration of Δ9-THC and other psychoactive cannabinoids were minimally observed with ultrapure ajulemic acid. While JBT-101 increased ring immobility, it did so only at higher doses (30 and 56 mg/kg). Together, these results demonstrate that the effects of JBT-101 differ from those of earlier syntheses of (non-purified) ajulemic acid. In conclusion, the pharmacological profile of JBT-101 is consistent with it being a CB2 selective compound with little CB1 receptor activity.

Example 4

Binding Curves of Selected Cannabinoids for CB2 and CB1

FIG. 12 shows the binding curves for ultrapure AJA and reference cannabinoid antagonists selective for CB2 and CB1.

CB Receptor Binding Assays

Membrane preparation—HEK-293T cells were cultured according to ATCC (Manassas, Va.) guidelines and transfected with human CB1 cDNA (Genbank X54937) or CB2 cDNA (Genbank X74328), operably linked to the SV40 promoter, using Polyfect (Qiagen, Valencia, Calif.) or Fugene (Roche, Nutley, N.J.) according to manufacturer's instructions. 48 h after transfection, cells were harvested in ice cold membrane buffer (20 mM HEPES, 6 mM MgCl2, 1 mM EDTA, pH 7.2) using a cell scraper. Cells were transferred to a nitrogen cavitation chamber and a pressure of 900 bar was applied for 30 min. The pressure was released and the cell debris was collected and centrifuged at 1000 g at 4° C. for 10 min. The supernatant was collected and the spin was repeated until the supernatant was free of precipitate. Membranes were then pelleted by centrifugation at 12,000 g at 4° C. for 20 min. Membranes were resuspended in an appropriate amount of membrane buffer. The membrane concentration was determined using a BioRad (Hercules, Calif.) protein assay dye reagent according to manufacturer's instructions. Membranes were diluted to 1 mg/ml and aliquots snap-frozen in liquid nitrogen and store at −80° C.

Binding assay—0.5-10 ng of membranes expressing human CB1 or human CB2 receptors were incubated in binding buffer (50 mM Tris, 10 mM MgCl$_2$, 1 mM EDTA, 0.1% BSA, pH 7.4) in the presence of 0.5 to 2 nM radioligand ([3H]-CP55940; Perkin Elmer except 3 nM [3H]-SR141716 was used as the radioligand where noted), and varying concentrations of ligands (total volume 200 μL/well of a 96 well plate). Membranes were incubated for 2 hr at room temperature, then filtered onto a presoaked (with 0.1% polyethylenimine for 1 to 2 hr) 96 well GF/B filterplate (Packard Bioscience, Shelton, Conn.) and washed with 500 mL ice cold wash buffer (25 mM HEPES, 1 mM CaCl$_2$, 5 mM MgCl$_2$, 0.25M NaCl) using a Filtermate 196 Harvester (Packard Instruments, Downers Grove, Ill.). The filter plates were dried before addition of 50 μL of scintillation fluid to each well (Microscint 20, Packard, Shelton, Conn.). Plates were counted on a Topcount NXT (Packard, Shelton, Conn.).

Data Analysis—Graphs were plotted and IC$_{50}$ values were determined by nonlinear regression analysis using Prism software (GraphPad version 4.0, San Diego, Calif., USA). Ki values were calculated from IC$_{50}$ values using the Cheng & Prussoff method using reported Ki values of 2.9 nM for SR141716 receptors for human CB1 receptors, and 2.5 nM and 0.92 nM for CP55,940 for human CB1 and human CB2 receptors, respectively (McPartland et al, BJP, 2007).

Example 5 Ultrapure AJA Induced CB2 Receptor-Mediated In Vivo Effects

Fibrosis Animal Model—Bleomycin Induced Skin Fibrosis

Groups of 8 mice (6-12 week-old C57Bl) received daily s.c. injections of bleomycin (20 ug/mouse) or vehicle for 14 days, followed by one weeks of recovery. In parallel, starting day 1, ultrapure AJA suspended in 2% methylcellulose (MC) or vehicle was administered by oral gavage at 0, 2.5, 5.0 and 10 mg/kg. On day 21, mice were sacrificed. Their skin was harvested and processed for routine histology (H&E, trichrome and picrosirius red stains), immunohistology (paraffin-embedded or frozen samples), in situ hybridization, collagen (SIRCOL) assays, and RNA isolation for real-time qPCR or microarray hybridization. Skin sections were carefully characterized and quantified for dermal inflammation, dermal thickening, collagen accumulation (Trichrome), and collagen cross-linking (Sirius red) in lesional skin.

Figure 18:
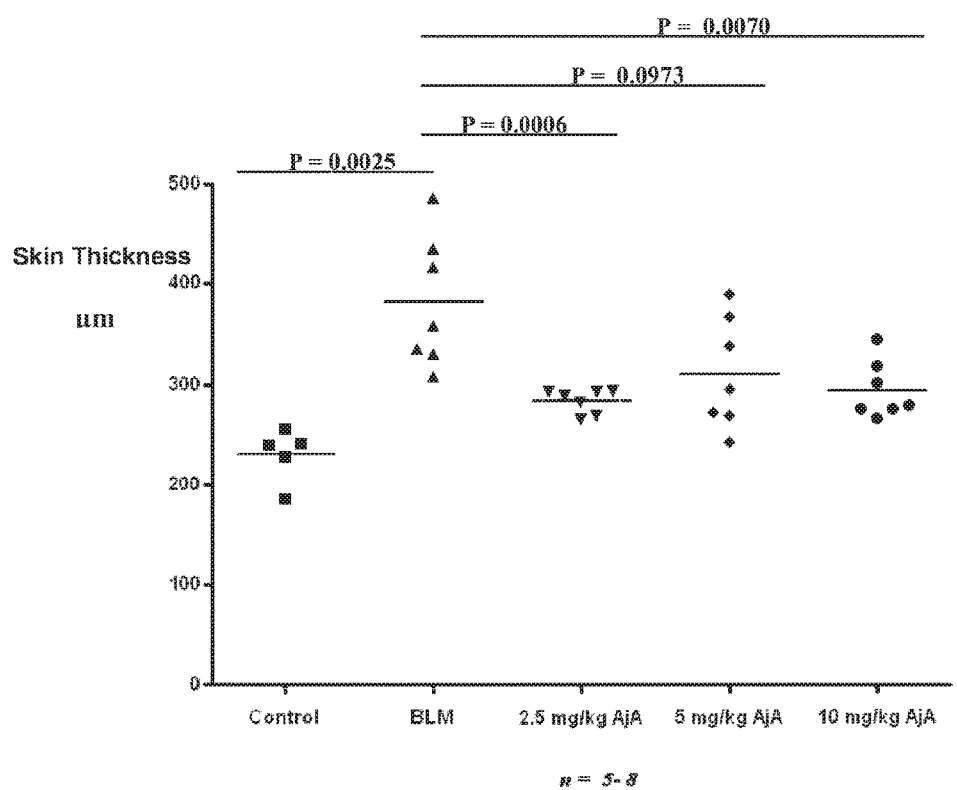
FIG. 18 shows that JBT-101 is effective at inhibiting skin fibrosis in the bleomycin mouse model of scleroderma, a CB2 dependent response. Mice were treated daily with local injection of bleomycin and administered orally the indicated doses of JBT-101 (ultrapure AJA). All doses, including a dose of 1 mg/kg (data not shown) were equally effective at inhibiting skin thickening.

Results: As seen in FIG. 18, ultrapure AJA was effective at all doses tested for inhibition of CB2 mediated skin fibrosis in the mouse belomycin model. These same doses were completely ineffective in the CB1 mediated behavioral models shown in FIGS. 14-16 supporting the maintenance of CB2 activity in ultrapure ajulemic acid in the absence of any CB1 activity.

Inflammation Animal Model—Paw Edema Model

CD-1 Mice (Female) were randomly allocated to experimental groups and allowed to acclimatise for one week. Prior to test compound administration, baseline right hind paw volume was measured under gas (isoflurane) anaesthesia using a water displacement device (plethysmometer, Stoelting). On Day 0, ultrapure AJA suspended in 2% MC or vehicle was administered at 0, 5, 50 and 500 ug/kg by oral gavage. Ninety minutes after treatment administration, the animals were given 10 microliters of a 100 mg/ml arachidonic acid solution in 5% ethanol by subcutaneous injection into the plantar aspect of the right hind paw. A control group of animals (Group 1) was administered with an equivalent volume of a 5% ethanol solution. The left hind paws were not injected. Intra-plantar injections were performed under gas anaesthesia. 45 minutes after the intra-plantar injections right hind paw volume was measured under gas anaesthesia using a plethysmometer.

Figure 19:
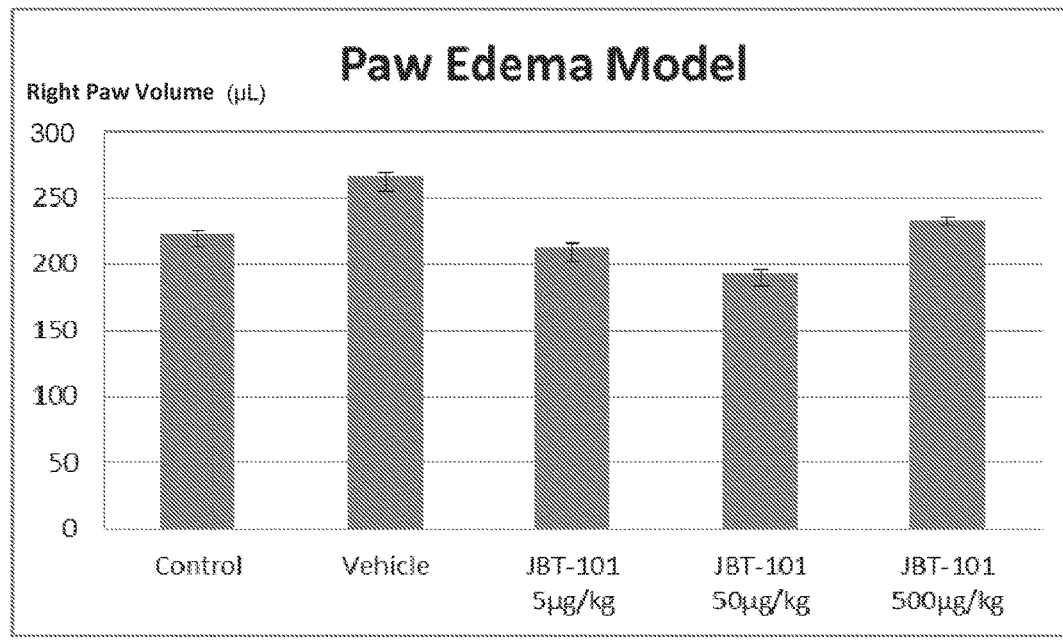
FIG. 19 shows that JBT-101 (ultrapure AJA) is effective at doses well below the doses in which CB1 activity is observed, at inhibiting paw volume in a model of arachidonic acid induced paw edema, a CB2 dependent response. Mice were administered orally the indicated doses of JBT-101 (ultrapure AJA) followed 90 minutes later with intra-planar injection of arachidonic acid in the right paw. Right paw volume was measured 45 minutes post-arachidonic acid injection.

Results: As seen in FIG. 19, ultrapure AJA was effective at all doses tested at inhibiting inflammation in the mouse paw edema model. These same doses were completely ineffective in the CB1 mediated behavioral models shown in FIGS. 14-16 supporting the maintenance of CB2 activity in ultrapure ajulemic acid in the absence of any CB1 activity.

REFERENCES

1. Stahl, P. H. and Wermuth, C. G., (Eds.) (2002) *Handbook of Pharmaceutical Salts: Properties Selection and Use*, Verlag Helvetica Chimica Acta/Wiley-VCH, Zurich.
2. Burstein, S. H.; Audette, C. A.; Breuer, A.; Devane, W. A.; Colodner, S.; Doyle, S. A.; Mechoulam, R. *J Med Chem* 1992, 35, 3135.3.
3. Dyson, A. et al. (2005) Antihyperalgesic properties of the cannabinoid CT-3 in chronic neuropathic and inflammatory pain states in the rat, *Pain* 116(1-2), 129-137.
4. Recht, L. D. et al. (2001) Antitumor effects of ajulemic acid (CT3), a synthetic non-psychoactive cannabinoid, *Biochem. Pharmacol.* 62(6), 755-763.
5. LeRoy, E. C. (1974) Increased Collagen Synthesis by Scleroderma Skin Fibroblasts in Vitro a Possible Defect in the Regulation or Activation of the Scleroderma Fibroblast, *J. Clin. Invest.* 54(4), 880-889.
6. Welch, S. C. and Walters, M. E. (1978) Reduction of aryl diethyl phosphates with titanium metal: a method for deoxygenation of phenols, *The Journal of Organic Chemistry* 43(25), 4797-4799.
7. Wang, F., Chiba, K., and Tada, M. (1992) Facile deoxygenation of phenols and enols using sodium borohydride-nickel chloride, *Journal of the Chemical Society, Perkin Transactions* 1(15), 1897-1900.
8. Saa, J. M. et al. (1990) Deoxygenation of highly hindered phenols, *The Journal of Organic Chemistry* 55(3), 991-995.
9. Rowe, R. C. (2009) *Handbook of Pharmaceutical Excepients*, 6th ed., Pharmaceutical Press.
10. Pertwee, R. G et al. (2010) International Union of Basic and Clinical Pharmacology. LXXIX. Cannabinoid Receptors and Their Ligands: Beyond CB1 and CB2, *Pharmacol. Rev.* 62(4), 588-631.
11. Burstein, S. H. et al. (1992) Synthetic nonpsychotropic cannabinoids with potent antiinflammatory, analgesic, and leukocyte antiadhesion activities, *J Med Chem* 35(17), 3135-3141.
12. Recht, L. D. et al. (2001) Antitumor effects of ajulemic acid (CT3), a synthetic non-psychoactive cannabinoid, *Biochem Pharmacol* 62(6), 755-763.
13. Karst, M. et al. (2003) Analgesic effect of the synthetic cannabinoid CT-3 on chronic neuropathic pain: a randomized controlled trial, *Jama* 290(13), 1757-1762.
14. Rhee M-H, Vogel Z, Barg J, Bayewitch M, Levy R, Hanus L, Breuer A, and Mechoulam R. Cannabinol Derivatives: Binding to Cannabinoid Receptors and Inhibition of Adenylylcyclase. J. Med. Chem. 1997, 40, 3228-3233.
15. McPartland J M, Glass M, Pertwee R G. Meta-analysis of cannabinoid ligand binding affinity and receptor distribution: interspecies differences. Br J Pharmacol. 2007 November; 152(5):583-93
16. Cheng Y, Prusoff W H. Relationship between the inhibition constant (Ki) and the concentration of inhibitor which causes 50 percent inhibition ($IC_{50}$) of an enzymatic reaction. Biochem Pharmacol. 1973 Dec. 1; 22(23):3099-108.
17. U.S. Pat. No. 5,338,753. S. Burstein and R. Mechoulam. (3R, 4R)-Δ6-THC-7-oic acids useful as antiinflammatory agents and analgesics. (August, 1994).
18. Weiland et al., (1994) Measurement of receptor-stimulated guanosine-5'-O-(γ-thio)triphosphate binding by G proteins. Methods Enzymol 237:3-13.
19. Griffin et al., Evaluation of Cannabinoid Receptor Agonists and Antagonists Using the Guanosine-5'-O-(3-[35S]thio)-triphosphate Binding Assay in Rat Cerebellar Membranes, JPET 285:553-560, 1998.
20. Wiley et al., Structural and pharmacological analysis of 0-2050, a putative neutral cannabinoid CB(1) receptor antagonist, Eur. J. Pharmacol. 2011, 651(1-3):96-105.
21. Wiley J L and Martin B R, Cannabinoid pharmacological properties common to other centrally acting drugs, Eur. J. Pharmacol. 2003, 471(3):185-193
22. Burstein, et al. Synthetic non-psychotropic cannabinoids with potent anti-inflammatory, analgesic and leukocyte anti adhesion activities. J. Med. Chem., 35:3135-3141 (1992).

We claim:

1. A method of ameliorating one or more symptoms of an inflammatory disease in a subject in need thereof, wherein the inflammatory disease is dermatomyositis, the method comprising administering to the subject a pharmaceutical composition comprising one or more cannabinoids, wherein said one or more cannabinoids comprise at least 98% (w/w) (6aR,10aR)-3-(1',1'-dimethylheptyl)-Δ8-tetrahydro-cannabinol-9-carboxylic acid (ajulemic acid), or a pharmaceutically acceptable salt thereof, and wherein no significant antinociception is observed in a hot plate test of mice following oral administration to the mice of 10 mg/kg of said one or more cannabinoids.

2. The method of claim 1, wherein said pharmaceutical composition is administered orally, intravenously, topically, interstitially, by inhalation, via an implant, via a patch, or by ophthalmic administration.

3. The method of claim 2, wherein said pharmaceutical composition is administered orally.

4. The method of claim 2, wherein said pharmaceutical composition is administered topically.

5. The method of claim 2, wherein said pharmaceutical composition is administered by ophthalmic administration.

6. The method of claim 2, wherein said pharmaceutical composition is administered intravenously.

7. The method of claim 2, wherein said pharmaceutical composition is administered by inhalation.

8. The method of claim 1, wherein said pharmaceutical composition is administered in combination with one or more compounds.

9. The method of claim 1, wherein said subject is a human.

10. The method of claim 1, wherein said subject is non-human animal.

11. The method of claim 10, wherein said non-human animal is a dog or a cat.

12. The method of claim 1, wherein said pharmaceutical composition is a unit dosage formulation comprising about 0.5 mg to about 120 mg of said (6aR,10aR)-3-(1',1'-dimethylheptyl)-Δ8-tetrahydro-cannabinol-9-carboxylic acid, or a pharmaceutically acceptable salt thereof, and wherein said unit dosage formulation is administered once daily.

13. The method of claim 1, wherein said pharmaceutical composition is a unit dosage formulation comprising about 0.15 mg to about 40 mg of said (6aR,10aR)-3-(1',1'-dimethylheptyl)-Δ8-tetrahydro-cannabinol-9-carboxylic acid, or a pharmaceutically acceptable salt thereof, and wherein said unit dosage formulation is administered up to three times daily.

14. The method of claim 1, wherein said one or more cannabinoids comprise at least 99% (w/w) (6aR,10aR)-3-(1',1'-dimethylheptyl)-Δ8-tetrahydro-cannabinol-9-carboxylic acid (ajulemic acid).

15. The method of claim 1, wherein said one or more cannabinoids comprise less than 0.5% (w/w) 11-hydroxy-(6aR,10aR)-3-(1',1'-dimethylheptyl)-Δ8-tetrahydro-cannabinol (HU-210).

16. The method of claim 15, wherein said one or more cannabinoids comprise less than 0.1% (w/w) 11-hydroxy-(6aR,10aR)-3-(1',1'-dimethylheptyl)-Δ8-tetrahydro-cannabinol (HU-210).

* * * * *